(12) United States Patent
Heaney et al.

(10) Patent No.: US 7,097,829 B2
(45) Date of Patent: Aug. 29, 2006

(54) TRANSGENIC CELLS TRANSFECTED WITH PITUITARY TUMOR TRANSFORMING GENE (PTTG)) EXPRESSION VECTORS AND USES THEREFOR

(75) Inventors: Anthony P. Heaney, Los Angeles, CA (US); Shlomo Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 354 days.

(21) Appl. No.: 10/264,372

(22) Filed: Oct. 4, 2002

(65) Prior Publication Data

US 2003/0100530 A1 May 29, 2003

Related U.S. Application Data

(63) Continuation-in-part of application No. 09/854,326, filed on May 11, 2001, which is a continuation-in-part of application No. 09/777,422, filed on Feb. 5, 2001, now abandoned, which is a continuation-in-part of application No. 09/730,469, filed on Dec. 4, 2000, now abandoned, which is a continuation-in-part of application No. 09/687,911, filed on Oct. 13, 2000, now abandoned, which is a continuation-in-part of application No. 09/569,956, filed on May 12, 2000, now Pat. No. 6,894,031, which is a continuation-in-part of application No. 08/894,251, filed as application No. PCT/US97/21463 on Nov. 21, 1997, now Pat. No. 6,455,305.

(60) Provisional application No. 60/031,338, filed on Nov. 21, 1996.

(51) Int. Cl.
  *A01N 63/00* (2006.01)
  *C12N 15/00* (2006.01)
  *C12N 15/63* (2006.01)
  *C07H 21/04* (2006.01)

(52) U.S. Cl. ............ 424/93.21; 424/93.2; 435/320.1; 435/455; 536/23.5

(58) Field of Classification Search ............ 424/93.2, 424/93.21; 435/320.1, 455; 536/23.5
See application file for complete search history.

(56) References Cited

U.S. PATENT DOCUMENTS

| | | | |
|---|---|---|---|
| 5,171,674 A | 12/1992 | Stevens et al. | |
| 5,474,897 A | 12/1995 | Weiss et al. | 435/6 |
| 5,500,343 A | 3/1996 | Blum et al. | |
| 5,552,390 A | 9/1996 | Scholar et al. | |
| 5,608,148 A | 3/1997 | John | |
| 5,684,222 A | 11/1997 | Mak | |
| 5,714,667 A | 2/1998 | Waterhouse et al. | |
| 5,801,154 A | 9/1998 | Baracchini et al. | |
| 5,807,746 A | 9/1998 | Lin et al. | |
| 5,814,300 A | 9/1998 | Scott et al. | |
| 5,831,066 A | 11/1998 | Reed | |
| 5,837,469 A | 11/1998 | Harris | |
| 5,843,404 A | 12/1998 | Koch et al. | |
| 5,844,107 A | 12/1998 | Hanson et al. | 536/23.1 |
| 5,877,302 A | 3/1999 | Hanson et al. | 526/23.1 |
| 5,972,900 A | 10/1999 | Ferkol, Jr. et al. | 514/44 |
| 5,972,901 A | 10/1999 | Ferkol, Jr. et al. | 514/44 |
| 6,046,028 A | 4/2000 | Conklin et al. | |
| 6,069,008 A | 5/2000 | Bennett et al. | |
| 6,072,041 A | 6/2000 | Davis et al. | 530/390.1 |
| 6,077,835 A | 6/2000 | Hanson et al. | 514/44 |
| 6,087,555 A | 7/2000 | Dunstan et al. | |
| 6,107,091 A | 8/2000 | Cowsert | |
| 6,136,040 A | 10/2000 | Ornitz et al. | |
| 6,566,127 B1 | 5/2003 | Pavco et al. | |
| 2003/0130219 A1 | 7/2003 | Horwitz et al. | |
| 2003/0186910 A1 | 10/2003 | Horwitz et al. | |

FOREIGN PATENT DOCUMENTS

| | | |
|---|---|---|
| JP | 7322892 A2 | 12/1995 |
| JP | 9173053 A2 | 7/1997 |
| WO | WO 90/09442 | 8/1990 |
| WO | WO 93/25712 | 12/1993 |
| WO | WO 95/25809 | 9/1995 |
| WO | WO 98/22587 | 5/1998 |
| WO | WO 98/39412 | 9/1998 |

OTHER PUBLICATIONS

Kaye et al., 1990, Proc. Natl. Acad. Sci. USA, vol. 87, pp. 6922-6926.*
Davis, C. G., 1990, The New Biologist, vol. 2, No. 5, p. 410-419.*
Skolnick et al., 2000, Trends in Biotech, vol. 18, p. 34-39.*
Deonarain,, M., 1998, Expert Opin. Ther. Pat., vol. 8, pp. 53-69.*
Eck et al., 1996, Goodman & Gilman's The Pharmacological Basis of Therapeutics, McGraw-Hill, New York, p. 77-101.*
Gorecki, D., 2001, Expert Opin. Emerging Drugs, 6(2): 187-198.*

(Continued)

*Primary Examiner*—Shin-Lin Chen
(74) *Attorney, Agent, or Firm*—Seth D. Levy; Davis Wright Tremaine LLP

(57) ABSTRACT

Described are cells transfected with expression vectors containing pituitary tumor transfer gene (PTTG) and uses therefor. The PTTG nucleic acids may be operatively linked to a vector, optionally provided with control and expression sequences, and/or may be carried by a host cell. The host cell may be a thyroid stimulating hormone (TSH)-sensitive cell transfected with an expression vector comprising a DNA segment encoding functional PTTG, wherein the cell overexpresses PTTG in response to TSH. Also described is an in vitro cell model used to study biological processes mediated by PTTG and a method for evaluating a compound for its ability to modulate PTTG expression.

12 Claims, 8 Drawing Sheets

OTHER PUBLICATIONS

PCT International Search Report—PCT/US 97/21463, Nov. 22, 1997.

Marra, M., et al., "The WashU-HHMI Mouse EST project, AC W81747", EMBL Database, Jun. 27, 1996, Heidelberg, XP002066845.

Hillier, L., et al., The WashU-Merck EST project, AC AA007646, EMBL Database, Jul. 28, 1996, Heidelberg, XP002066846.

Holton, T., et al., "ACQ57612", EMBL Database, Sep. 5, 1994, Heidelberg, XP002066847.

Nippon Telegraph and Telephone Corp.: "ACQ75553", EMBL Database, Aug. 4, 1995, Heidelberg, XP002066848.

Gonsky, R., et al., "Transforming DNA Sequences Present in Human Prolactin-Secreting Pituitary Tumors", Molec. Endocrin., 5(11): 1687-1695, Nov. 1991.

Pei, L., et al., "Isolation and Characterization of a Pituitary Tumor-Transforming Gene (PTTG)", Molec. Endocrin., 11(4): 433-441, Apr. 1997.

Shimon, I., et al., "Genetic Basis of Endocrine Disease", J. Clin. Endocrin. And Metab., 82(6): 1675-1681, Jun. 1997.

Chen, L., et al., "Identification of the human pituitary tumor transforming gene (hPTTG) family: molecular structure, expression, and chromosomal localization.", 1: Gene May 2, 2000; 248 (102): 41-50. Abstract Only.

Heaney, A.P., "Expression of pituitary-tumor transforming gene in colorectal tumours", 1: Lancet Feb. 26, 2000: 355(9205): 716-9.

Heaney, A.P., "Early Involvement of Estrogen-induced pituitary tumor transforming gene and fibroblast growth factor expression in prolactinoma pathogenesis", 1: Nat Med Nov. 1999; 5(11): 1317-21.

Suhardja, A.S., et al., "Molecular pathogenesis of pituitary adenomas: a review.", Acta Neurochir (Wien) 1999; 141(7): 729-36. Abstract Only.

Ren, R., et al., "Identification of a ten-amino acid proline-rich SH3 binding site.", Science Feb. 19, 1993; 259(5098): 1157-61. Abstract Only.

Liu, X., et al., "The v-Src SH3 domain binds phosphatidylinositol 3'-kinase.", Mol Cell Biol Sep. 1993; 13(9): 5225-32. Abstract Only.

Gout, I., et al., "The GTPase dynamin binds to and is activated by a subset of SH3 domains." Cel Oct. 8, 1993; 75(1): 25-36.

Yu, H., et al., "Solution structure of the SH3 domain of Src and identification of its ligan-binding site." Science Dec. 4, 1992; 258(5088): 1665-8. Abstract Only.

Lee, I.A., et al., "Cloning and expression of human cDNA encoding human homologue of pituitary tumor transforming gene.", Biochem Mol. biol Int May 1999; 47(5): 891-7. Abstract Only.

Zou, H., et al., "Identification of a vertebrate sister-chromatid separation inhibitor involved in transformation and tumorigenesis.", Science Jul. 16, 1999; 285(5426): 418-22. Abstract Only.

Zhang, X., et al., "Pituitary tumor transforming gene (PTTG) expression in pituitary adenomas." J. Clin Endocrinol Metab Feb. 1999; 84(2): 761-7.

Prezant, T.R., et al., "An intronless homolog of human proto-oncogene hPTTG is expressed in pituitary tumors; evidence for hPTTG family.", J Clin Endocrinol Metab Mar. 1999; 84(3): 1149-52.

Fujimoto, N., et al., "Establishment of an estrogen responsive rat pituitary cell sub-line MtTE-2." Endocr J Jun. 1999; 46(3): 389-96. Abstract Only.

Ramos-Morales, F., et al., "Cell cycle regulated expression and phosphorylation of hpttg proto-oncogene product.", Oncogene Jan. 20, 2000; 19(3): 403-9. Abstract Only.

McCabe C.J., et al., "PTTG—a new pituitary tumour transforming gene.", J Endocrinol Aug. 1999; 162(2): 163-6. Abstract Only.

Kakar, S.S., "Molecular cloning, genomic organization, and identification of the promoter for the human pituitary tumor transforming gene (PTTG).", Gene Nov. 29, 1999; 240(2): 317-24. Abstract Only.

Dominguez, A., et al., "hpttg, a human homologue of rat pttg, is overexpressed in hematopoietic neoplasms. Evidence for a transcriptional activation function of hPTTG.", Oncogene Oct. 29, 1998; 17(17): 2187-93. Abstract Only.

Pei, L., "Pituitary tumor-transforming gene protein associates with ribosomal protein S10 and a novel human homologue of DnaJ in testicular cells.", J Biol Chem Jan. 29, 1999; 274(5): 3151-8.

Saez, C., et al., "hpttg is over-expressed in pituitary adenomas and other primary epithelial neoplasias.", Oncogene Sep. 23, 1999; 18(39): 5473-6. Abstract Only.

Pei, L., "Genomic Organization and identification of an enhancer element containing binding sites for multiple proteins in rat pituitary tumor-transforming gene.", J Biol Chem Feb. 27, 1998; 273(9): 5219-25.

Wang, Z., et al., "Characterization of the murine pituitary tumor transforming gene (PTTG) and its promoter.", Endocrinology Feb. 2000; 141(2): 763-71.

Zhang, X., et al., "Structure, expression, and function of human pituitary tumor-transforming gene (PTTG).", Mol Endocrinol Jan. 1999; 13(1): 156-66.

Heaney, Anthony, P., et al., "Pituitary tumor transforming gene: a novel factor in pituitary tumour formation," Balliere's Clinical Endocrinology and Metabolism, vol. 13, No. 3, pp. 367-380, 1999.

Freeman, G. J. et al., Engagement of the PD-1 Immunoinhibitory receptor by a Novel B7 family Member Leads to Negative Regulation of Lymphocyte Activation, J. Exp Med, 192(7):1027-1034 (Oct. 2, 2000). Abstract Only.

George, J. et al., Adoptive Transfer of beta (2)-Glycoprotein I-Reactive Lymphocytes Enhances Early Atherosclerosis in LDL Receptor-Deficient Mice, Circulation, 102(15):1822-1827 (Oct. 10, 2000). Abstract Only.

Griffin, J. M. et al., CD4 (+) T-Cell Activation and Induction of Autoimmune Hepatitis following Trichloroetheylene Treatment in MRL+/+Mice, Toxicol Sci, 57(2):345-352 (Oct. 2000). Abstract Only.

Grom, A. A. et al., T-cell and T-cell receptor abnormalities in the immunopathogenesis of juvenile theumatoid arthritis, Curr Opin Rheumatol, 12(5):420-4 (Sep. 2000). Abstract Only.

Han, W. R. et al., Prolonged allograft survival in anti-CD4 antibody transgenic mice: lack of residual helper T cells compared with other CD4-deficient mice, 70(1):168-74 (Jul. 15, 2000). Abstract Only.

Hotchkiss, R. S. et al., Rapid onset of intestinal epthelial and lymphocyte apoptotic cell death in patients with trauma and shock, Crit Care Med, 28(9):3207-17 (Sep. 2000). Abstract Only.

Karandikar, N. J. et al., CTLA-4 downregulates eptitope spreading and mediates remission in relapsing experimental autoimmune encephalomyelitis, J. Neuroimmunol, 109(2):173-80 (sep. 2000). Abstract Only.

Kenyon, N. J. et al., Enhanced cytokine generation by peripheral blood mononuclear cells in allergic and asthma subjects, Ann Allergy Asthma Immunol, 85(2):115-20 (Aug. 2000). Abstract Only.

Kerlero de Rosbo, N et al., Rhesus monkeys are highly susceptible to experimental autoimmune encephalomyelitis induce by myelin oligodendrocyte glycoprotein: characterisation of immunodominant T-and B-cell epitopes, J. Neuroimmunol, 110(1-2):83-96. (Oct. 2, 2000). Abstract Only.

Krieger, N. R. et al., Rat pancreatic islet and skin xenograft survival in CD4 and CD8 knockout mice, J. Autoimmun, 10(3):309-15 (Jun. 1997). Abstract Only.

McCabe, C. J. et al., PTTG—a new pituitarty tumour transforming gene, Journal of Endocrinology, vol. 162, pp. 163-166 (1999).

Nakajima, A. et al., Involvement of CD70-CD27 interactions in the induction of experimental autoimmune encephalomyelitis, J Neuroimmunol, 109(2):188-96 (Sep. 22, 2000). Abstract Only.

Nickoloff, B. J. et al., Is psoriasis a T-cell disease?, Exp Dermatol, 9(5):359-75 (Oct. 2000). Abstract Only.

Odaka, C. et al., Angiotensin-converting enzyme inhibitor captopril prevents activation—induced apoptosis by interfering with T cell activation signals, Clin Exp Immunol, 121(3):515-22 (Sep. 2000). Abstract Only.

Oliver, J. M. et al., Immunologically mediated signaling in basophils and mast cells: finding therapeutic tartgets for allergic diseases in the human FcvarepsilonRl signaling pathway, Immunopharmacology, 48(3):269-281 (Jul. 25, 2000). Abstract Only.

Ott, V. L. et al., *Activating and inhibitory signaling in mast cells: New opportunities for therapeutic intervention?*, J Allergy Clin Immunol, 106(3 Pt 1):429:440 (Sep. 2000). Abstract Only.

Simeonovic, C. J. et al., *Differences in the contribution of CD4+ T Cells to proislet and islet allograft rejection correlate with constitutive class II MHC alloantigen expression*, Cell Transplant, 5(5):525-41 (Sep.-Oct. 1996). Abstract Only.

Uchida, T. et al., *Roles of CD4+ and CD8+ T cells in discordant skin xenograft rejection*, Transplantation, 68(11):1721-7 (Dec. 1999). Abstract Only.

Wang, H. B. et al., *Tumor necrosis factor receptor-l is critically involved in the development of experimental autoimmune myasthenia gravis*, Int Immunol, 12(10):1381-1388 (Oct. 2000). Abstract Only.

Wang, Z. et al., *Pituitary tumor transforming gene (PTTG) transforming and transactivation activity*, J Biol Chem, 275(11)L7459-61 (Mar. 17, 2000).

Yi, S. et al., *CD8+ T cells are capable of rejecting pancreatic islet xenografts*, Transplantation, 70(6):896-906 (Sep. 27, 2000). Abstract Only.

Dubik, D. et al., *Mechanism of estrogen activation of c-myc oncogene expression*, Oncogene 7(8):1587-94 (Aug. 1992). Abstract Only.

Farrell WE, *Molecular Pathogenesis of Pituitary Tumors*, Front Neuroendocrinol, 21 (3):174-198 (Jul. 2000) Abstract Only.

Levin, Ellis R., *Cellular Functions of the Plasma Membrane Estrogen Receptor*,TEM vol. 10, No. 9, pp. 374-377 (1999).

Pei L, *Activiation of mitogen-activated kinase cascade regulates pituitary tumor-transforming gene transactivation function*, J. Biol Chem [epub ahead of print] (Jul. 21, 2000) Abstract Only.

Petz, Larry N, et al, *Spl Binding Sites and an Estrogen Response element Half-site Are Involved in Regulation of the Human Progesterone Receptor A Promoter*, Molecular Endocrinology, 14:972-985 (2000).

Porter, W., et al., *Functional Synergy between the Transcription Factor Spl and the Estrogen Receptor*, Molecular Endocrinology, 11:1569-1580 (1997).

Ramos-Morales F., et al., *Cell cycle regulated expression and phosphorylation of hpttg proto-oncogene product*, Oncogene 19 (3):403-9 (Jan. 20, 2000) Abstract Only.

Shepel LA, et al., *Relationship of polymorphisms near the rat prolactin, N-ras, and retinoblastoma genes with susceptibility to estrogen-induced pituitary tumors*, Cancer Res, 50 (24):7920-5. (Dec. 15, 1990) Abstract Only.

Sutherland, R. L, et al., *Estrogen and progestin regulation of cell cycle progression*, J Mammary Gland Biol Neoplasia 3 (1):63-72 (Jan. 1998) Abstract Only.

Wang, Zhiyong, et al., *Characterization of the Murine Pituitary Tumor Transforming gene (PTTG) and Its Promoter*, Endocrinology, 141:763-771 (2000).

Wu-Peng, Sharon X., et al., et al., *Delineation of Sites Mediating Estrogen Regulation of the Rat Creatine Kinase B Gene*, Molecular, Endocrinology 6:231-240 (1992).

Auerbach, R. et al., *Assays for Angiogenesis: A Review*, Pharmac. Ther., 51:1-11 (1991).

Bikfalvi, A. et al., *Biological Roles of Fibroblast Growth Factor-2*, Endocrine Reviews, 18(1):26-45 (1997).

Darland, D. C. and D'Amore, P., *Blood vessel maturation: vascular development comes of age*, Journal of Clinical Investigation, 103(2):157-158 (1999).

Ferrara, N. and Davis-Smith, T., *The Biology of Vascular Endothelial Growth Factor*, Endocrine Reviews, 18(1):4-25 (1997).

Folkman, J. and Shing, Y.,*Angiogenesis*, Journal of Biological Chemistry, 267(16):10931-10934 (1992).

Hanahan, D. and Folkman, J., *Patterns and Emerging Mechanisms of the Angiogenic Switch During Tumorigenesis*, Cell, 86:353-364 (1996).

Horak, E. R. et al., *Angiogenesis, assessed by platelet/endothelial cell adhesion molecule antibodies, as indicator of node metastases and survival in breast cancer*, The Lancet, 340:1120-1124 (1992).

Jain, R. K. et al., *Quantitative angiogenesis assays: progress and problems*, Nature Medicine, 3:1203-1208 (1997).

Linderholm, B. et al., *Vascular Endothelial Growth Factor is of High Prognostic Value in Node-Negative Breast Carcinoma*, Journal of Clinical Oncology, 16(9):3121-3128 (1998).

Relf, M. et al., *Expression of the Angiogenic Factors Vascular Endothelial Cell Growth Factor, Acidic and Basic Fibroblast Growth Factor, Tumor Growth Factor β-1, Platelet-derived Endothelial Cell Growth Factor, Placenta Growth Factor, and Pleiotrophin in Human Primary Breast Cancer and Its Relation to Angiogenesis*, Cancer Research, 57:963-969 (1997).

Seghezzi, G. et al., *Fibroblast Growth Factor-2 (FGF-2) Induces Vascular Endothelial Growth Factor (VEGF) Expression in the Endothelial Cells of forming Capillaries: An Autocrine Mechanism Contributing to Angiogenesis*, Journal of Cell Biology, 141(7):1659-1673 (1998).

Takahashi, Y. et al., *Expression of Vascular Endothelial Growth Factor and Its Receptor, KDR, Correlates with Vascularity, Metastasis, and Proliferation of Human Colon Cancer*, Cancer Research, 55:3964-3968 (1995).

Weidner, N. et al., *Tumor Angiogenesis: A New Significant Independent Prognostic Indicator in Early-Stage Breast Carcinoma*, Journal of the National Cancer Institute, 84(24):1875-1887 (1992).

Aust et al.; Differential regulation of granulocyte-macrophage colony-stimulating factor mRNA and protein expression in human thyrocytes and thyroid-derived fibroblasts by interleukin-1α and tumour necrosis factor-α; Journal of Endocrinology; Nov. 1996, vol. 151, No. 2, pp. 277-285, especially abstract.

Databas Geneseq on STN, Accession No. AAV36963, Melmed et al., New pituitary tumor transforming gene and protein—used for diaagnosis, monitoring and treatment of tumours; WO9822587-A2, May 1998, computer printout pp. 1-2.

Eggo, et al., "Human Thyroid Cells Transfected with SV40 DNA Retain the TSH Receptor," Hormone and Metabolic Research Supplement Series, p. 68-71, ( 1990).

Accession No. H66067, 1995.

Chen, Leilei et al., Identification of the human pituitary tumor transforming gene (hPTTG) family: molecular structure, expression, and chromosomal localization, Gene, vol. 248, pp. 41-50 (2000), XP-002193233.

Crystal; Transfer of Genes to Humans: Early Lessons and Obstacles to Success, Science, vol. 270, pp. 404-410 (1995).

Cushman et al., "Molecular Basis of Pituitary Dysfunction in Mouse and Human," Mammalian Genome. Jul. 2001, vol. 12, No. 7, pp. 485-494.

Hillier, et al., ACC. H66113, Oct, 18, 1995.

Hillier, et al., Ernest 15: Hsa07621, AC AA007621 (a.a.).

Hillier, et al., Ernest 17: Hsn93319, AC N93319 (a.a.).

Hillier, et al., Ernest 14: Hs693284, AC N53693 (a.a.).

Hillier, L. et al., The WashU-Merck EST project, AC AA007646, EMBL Database, Jul. 28, 1996, Heidelberg, XP002066848.

Houdebine, L-M, 2002 , Journal of Biotechnology, vol. 98, p. 145-160.

Ishikawa, H., et al., "Human pituitary tumor-transforming gene induces angiogenesis," J. Clin. Endocrinology & Metabolism, vol. 86(2), pp. 867-874, (Feb. 2001). XP-002186233, Abstract Only.

Kappel et al., 1992 , Current Opinion in Biotechnology, vol. 3, p. 548-553.

Lord et al. (Cancer Res. 1993 Dec. 1;53(23):5721-6., abstract).

Marra, M. et al., Ernest 19: Mma14315, AC AA014315 (a.a.).

Marra, M. et al., Ernest 18: Mm01334, AC W67013 (a.a.).

Mei, J., et al. Securin is not required for cellular viability, but is required for normal growth of mouse embryonic fibroblasts, Current Biology, 11:1197-1201 (2001).

Ohgi et al.; Expression of Rnase Rh from *Rhizopus niveus* in Yeast and Characterization of the Secreted Proteins, J. Biochem, vol. 1, pp. 775-785 (1991).

Rudinger; Characteristics of the amino acids as components of a peptide hormone sequence, Peptide Hormones, pp. 1-7 (1976).

Sigmund, C., 2000, Arterioscler Thromb Vasc Biol., vol. 20, p. 1425-1429.

Sirawaraporn et al., The Journal of Biological Chemistry, 1993, 268(12): 8888-8892.

Sirawaraporn et al., PIR Accession No. A46049, 1993, p. 14.

Suzuki et al., 1995, Nucleic Acids Research, vol. 23, No. 22, p. 4664-4669.

Suzuki et al., Swissprot Accession No. p51510, p. 8.

Tarabykin, V., et al., "Expression of PTTG and prcl during telencephalic neurogenesis," Mech.Dev. 92(2):301-04 (Apr. 2000) Abstract Only.

Taylor et al., Antisense oligonucleotides: a systematic high-throughput approach to target validation and gene function determination, Dec. 1999, DDT, vol. 4 , No. 12, pp. 562-567.

Verma et al., 1997, Nature, vol. 389, p. 239-242.

Yu, R., et al., Pituitary Tumor Transforming Gene (PTTG) regulates placental JEG-3 cell division and survival: evidence from live cell imaging, Mol.Endocrinol. 14(8): 1137-46, (Aug. 2000) Abstract Only.

* cited by examiner

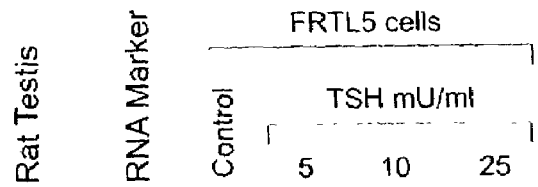
Fig. 5A
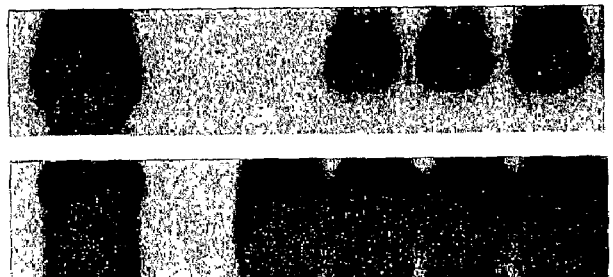
Fig. 5B
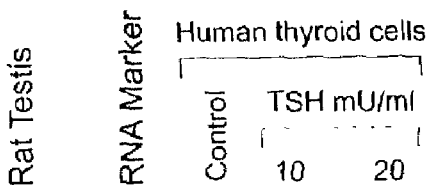
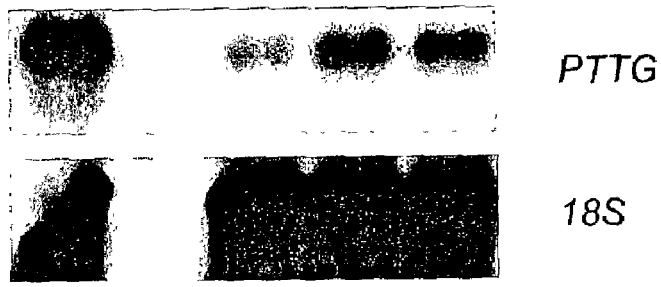
Fig. 5C
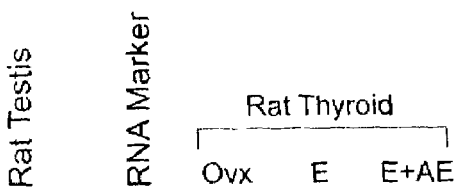
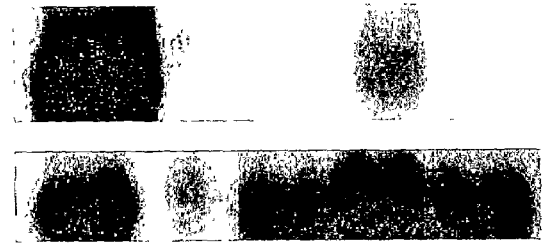

SEQUENCE LISTING

<160> NUMBER OF SEQ ID NOS: 6

<210> SEQ ID NO 1
<211> LENGTH: 974
<212> TYPE: DNA
<213> ORGANISM: Rattus rattus

<400> SEQUENCE: 1
aattcggcac gagccaacct tgagcatctg atcctcttgg cttctccttc ctatcgctga        60
gctggtaggc tggagacagt tgtttgggtg ccaacatcaa caaacgattt ctgtagttta       120

```
gcgtttatga cccctggcgtg aagatttaag gtctggatta agcctgttga cttctccagc    180
tacttctaaa ttttttgtgca taggtgctct ggtctctgtt gctgcttagt tcttccagcc    240
ttcctcaatg ccagttttat aatatgcagg tctctcccct cagtaatcca ggatggctac    300
tctgatcttt gttgataagg ataacgaaga gccaggcagc cgtttggcat ctaaggatgg    360
attgaagctg ggctctggtg tcaaagcctt agatgggaaa ttgcaggttt caacgccacg    420
agtcggcaaa gtgttcggtg ccccaggctt gcctaaagcc agcaggaagg ctctgggaac    480
tgtcaacaga gttactgaaa agccagtgaa gagtagtaaa cccctgcaat cgaaacagcc    540
gactctgagt gtgaaaaaga tcaccgagaa gtctactaag acacaaggct ctgctcctgc    600
tcctgatgat gcctacccag aaatagaaaa gttcttcccc ttcgatcctc tagattttga    660
gagttttgac ctgcctgaag agcaccagat ctcacttctc cccttgaatg gagtgcctct    720
catgatcctg aatgaagaga gggggcttga gaagctgctg cacctggacc cccccttcccc   780
tctgcagaag cccttcctac cgtgggaatc tgatccgttg ccgtctcctc ccagcgccct    840
ctccgctctg gatgttgaat tgccgcctgt ttgttacgat gcagatattt aaacgtctta    900
ctcctttata gtttatgtaa gttgtattaa taaagcattt gtgtgtaaaa aaaaaaaaaa    960
aaactcgaga gtac                                                      974
```

<210> SEQ ID NO 2
<211> LENGTH: 199
<212> TYPE: PRT
<213> ORGANISM: Rattus rattus

<400> SEQUENCE: 2

```
Met Ala Thr Leu Ile Phe Val Asp Lys Asp Asn Glu Glu Pro Gly Ser
 1               5                  10                  15

Arg Leu Ala Ser Lys Asp Gly Leu Lys Leu Gly Ser Val Lys Ala
            20                  25                  30

Leu Asp Gly Lys Leu Gln Val Ser Thr Pro Arg Val Gly Lys Val Phe
        35                  40                  45

Gly Ala Pro Gly Leu Pro Lys Ala Ser Arg Lys Ala Leu Gly Thr Val
    50                  55                  60

Asn Arg Val Thr Glu Lys Pro Val Lys Ser Lys Pro Leu Gln Ser
65                  70                  75                  80

Lys Gln Pro Thr Leu Ser Val Lys Lys Ile Thr Glu Lys Ser Thr Lys
                85                  90                  95

Thr Gln Gly Ser Ala Pro Ala Pro Asp Asp Ala Tyr Pro Glu Ile Glu
            100                 105                 110

Lys Phe Phe Pro Phe Asp Pro Leu Asp Phe Glu Ser Phe Asp Leu Pro
        115                 120                 125

Glu Glu His Gln Ile Ser Leu Leu Pro Leu Asn Gly Val Pro Leu Met
    130                 135                 140

Ile Leu Asn Glu Glu Arg Gly Leu Glu Lys Leu Leu His Leu Asp Pro
145                 150                 155                 160

Pro Ser Pro Leu Gln Lys Pro Phe Leu Pro Trp Glu Ser Asp Pro Leu
                165                 170                 175

Pro Ser Pro Pro Ser Ala Leu Ser Ala Leu Asp Val Glu Leu Pro Pro
            180                 185                 190

Val Cys Tyr Asp Ala Asp Ile
        195
```

<210> SEQ ID NO 3
<211> LENGTH: 779
<212> TYPE: DNA
<213> ORGANISM: Homo sapiens

<400> SEQUENCE: 3

```
atggccgcga gttgtggttt aaaccaggag tgccgcgcgt ccgttcaccg cggcctcaga      60
tgaatgcggc tgttaagacc tgcaataatc cagaatggct actctgatct atgttgataa     120
ggaaaatgga gaaccaggca cccgtgtggt tgctaaggat gggctgaagc tggggtctgg     180
accttcaatc aaagccttag atgggagatc tcaagtttca acaccacgtt ttggcaaaac     240
gttcgatgcc ccaccagcct tacctaaagc tactagaaag ctttgggaa ctgtcaacag      300
agctacagaa aagtctgtaa agaccaaggg acccctcaaa caaaaacagc caagcttttc     360
tgccaaaaag atgactgaga agactgttaa agcaaaaagc tctgttcctg cctcagatga     420
tgcctatcca gaaatagaaa aattctttcc cttcaatcct ctagactttg agagttttga     480
cctgcctgaa gagcaccaga ttgcgcacct ccccttgagt ggagtgcctc tcatgatcct     540
tgacgaggag agagagcttg aaaagctgtt tcagctgggc cccccttcac ctgtgaagat     600
gccctctcca ccatgggaat ccaatctgtt gcagtctcct tcaagcattc tgtcgaccct     660
ggatgttgaa ttgccacctg tttgctgtga catagatatt taaatttctt agtgcttcag     720
agtttgtgtg tatttgtatt aataaagcat tctttaacag ataaaaaaaa aaaaaaaa      779
```

<210> SEQ ID NO 4
<211> LENGTH: 202
<212> TYPE: PRT
<213> ORGANISM: Homo sapiens

<400> SEQUENCE: 4

```
Met Ala Thr Leu Ile Tyr Val Asp Lys Glu Asn Gly Glu Pro Gly Thr
  1               5                  10                  15

Arg Val Val Ala Lys Asp Gly Leu Lys Leu Gly Ser Gly Pro Ser Ile
             20                  25                  30

Lys Ala Leu Asp Gly Arg Ser Gln Val Ser Thr Pro Arg Phe Gly Lys
         35                  40                  45

Thr Phe Asp Ala Pro Pro Ala Leu Pro Lys Ala Thr Arg Lys Ala Leu
     50                  55                  60

Gly Thr Val Asn Arg Ala Thr Glu Lys Ser Val Lys Thr Lys Gly Pro
 65                  70                  75                  80

Leu Lys Gln Lys Gln Pro Ser Phe Ser Ala Lys Met Thr Glu Lys
                 85                  90                  95

Thr Val Lys Ala Lys Ser Ser Val Pro Ala Ser Asp Asp Ala Tyr Pro
            100                 105                 110

Glu Ile Glu Lys Phe Phe Pro Phe Asn Pro Leu Asp Phe Glu Ser Phe
        115                 120                 125

Asp Leu Pro Glu Glu His Gln Ile Ala His Leu Pro Leu Ser Gly Val
    130                 135                 140

Pro Leu Met Ile Leu Asp Glu Glu Arg Glu Leu Glu Lys Leu Phe Gln
145                 150                 155                 160

Leu Gly Pro Pro Ser Pro Val Lys Met Pro Ser Pro Trp Glu Ser
                165                 170                 175

Asn Leu Leu Gln Ser Pro Ser Ser Ile Leu Ser Thr Leu Asp Val Glu
            180                 185                 190

Leu Pro Pro Val Cys Cys Asp Ile Asp Ile
        195                 200
```

<210> SEQ ID NO 5
<211> LENGTH: 194
<212> TYPE: PRT
<213> ORGANISM: Mus musculus

<400> SEQUENCE: 5

| | | | | | | | | | | | | | | |
|---|---|---|---|---|---|---|---|---|---|---|---|---|---|---|
| Met | Ala | Thr | Leu | Ile | Phe | Val | Asp | Lys | Asp | Asn | Glu | Glu | Pro | Gly | Arg |
| 1 | | | | 5 | | | | | 10 | | | | | 15 | |
| Arg | Leu | Ala | Ser | Lys | Asp | Gly | Leu | Lys | Leu | Gly | Thr | Gly | Val | Lys | Ala |
| | | | 20 | | | | | 25 | | | | | 30 | | |
| Leu | Asp | Gly | Lys | Leu | Gln | Val | Ser | Thr | Pro | Arg | Val | Gly | Lys | Val | Phe |
| | | | 35 | | | | | 40 | | | | | 45 | | |
| Asn | Ala | Pro | Ala | Val | Pro | Lys | Ala | Ser | Arg | Lys | Ala | Leu | Gly | Thr | Val |
| | | 50 | | | | | 55 | | | | | 60 | | | |
| Asn | Arg | Val | Ala | Glu | Lys | Pro | Met | Lys | Thr | Gly | Lys | Pro | Leu | Gln | Pro |
| 65 | | | | | 70 | | | | | 75 | | | | | 80 |
| Lys | Gln | Pro | Thr | Leu | Thr | Gly | Lys | Lys | Ile | Thr | Glu | Lys | Ser | Thr | Lys |
| | | | | 85 | | | | | 90 | | | | | 95 | |
| Thr | Gln | Ser | Ser | Val | Pro | Ala | Pro | Asp | Asp | Ala | Tyr | Pro | Glu | Ile | Glu |
| | | | 100 | | | | | 105 | | | | | 110 | | |
| Lys | Phe | Phe | Pro | Phe | Asn | Pro | Leu | Asp | Phe | Asp | Leu | Pro | Glu | Glu | His |
| | | 115 | | | | | 120 | | | | | 125 | | | |
| Gln | Ile | Ser | Leu | Leu | Pro | Leu | Asn | Gly | Val | Pro | Leu | Ile | Thr | Leu | Asn |
| | 130 | | | | | 135 | | | | | 140 | | | | |
| Glu | Glu | Arg | Gly | Leu | Glu | Lys | Leu | Leu | His | Leu | Gly | Pro | Pro | Ser | Pro |
| 145 | | | | | 150 | | | | | 155 | | | | | 160 |
| Leu | Lys | Thr | Pro | Phe | Leu | Ser | Trp | Glu | Ser | Asp | Pro | Lys | Pro | Pro | Ser |
| | | | | 165 | | | | | 170 | | | | | 175 | |
| Ala | Leu | Ser | Thr | Leu | Asp | Val | Glu | Leu | Pro | Pro | Val | Cys | Tyr | Asp | Ala |
| | | | 180 | | | | | 185 | | | | | 190 | | |
| Asp | Ile | | | | | | | | | | | | | | |

<210> SEQ ID NO 6
<211> LENGTH: 945
<212> TYPE: DNA
<213> ORGANISM: Mus musculus

<400> SEQUENCE: 6

```
tcttgaactt gttatgtagc aggaggccaa atttgagcat cctcttggct tctctttata      60
gcagagattg taggctggag acagttttga tgggtgccaa cataaactga tttctgtaag     120
agttgagtgt tttatgaccc tggcgtgcag atttaggatc tggattaagc ctgttgactt     180
ctccagctac ttataaattt tgtgcatag gtgccctggg taaagcttgg tctctgttac      240
tgcgtagttt ttccagccgt tcaatgcca atattcaggc tctctccctt agagtaatcc      300
agaatggcta ctcttatctt tgttgataag gataatgaag aacccggccg ccgtttggca     360
tctaaggatg ggttgaagct gggcactggt gtcaaggcct tagatgggaa attgcaggtt     420
tcaacgcctc gagtcggcaa agtgttcaat gctccagccg tgcctaaagc cagcagaaag     480
gctttgggga cagtcaacag agttgccgaa aagcctatga agactggcaa acccctccaa     540
ccaaaacagc cgaccttgac tgggaaaaag atcaccgaga gtctactaa gacacaaagc      600
tctgttcctg ctcctgatga tgcctaccca gaaatagaaa agttcttccc tttcaatcct     660
ctagattttg acctgcctga ggagcaccag atctcacttc tccccttgaa tggcgtgcct     720
```

```
ctcatcaccc tgaatgaaga gagagggctg gagaagctgc tgcatctggg cccccctagc    780
cctctgaaga cacccttcct atcatgggaa tctgatccgc tgtactctcc tcccagtgcc    840
ctctccactc tggatgttga attgccgcct gtttgttacg atgcagatat ttaaacttct    900
tacttctttg tagtttctgt atgtatgttg tattaataaa gcatt                    945
```

TRANSGENIC CELLS TRANSFECTED WITH PITUITARY TUMOR TRANSFORMING GENE (PTTG)) EXPRESSION VECTORS AND USES THEREFOR

This application is a continuation-in-part of Ser. No. 09/854,326, filed May 11, 2001, which is a continuation-in-part of U.S. patent application Ser. No. 09/777,422, filed Feb. 5, 2001, now abandoned, which is a continuation-in-part of U.S. patent application Ser. No. 09/730,469, filed Dec. 4, 2000, now abandoned, which is a continuation-in-part of U.S. patent application Ser. No. 09/687,911, filed Oct. 13, 2000, now abandoned, which is a continuation-in-part of U.S. patent application Ser. No. 09/569,956, filed May 12, 2000, now issued as U.S. Pat. No. 6,894,031 on May 17, 2005, which is a continuation-in-part of U.S. patent application Ser. No. 08/894,251, filed Jul. 23, 1999, now issued as U.S. Pat. No. 6,455,305 on Sep. 24, 2002, as a national stage application, under 35 U.S.C. § 371, of international application PCT/US97/21463, filed Nov. 21, 1997, which claims the priority of the filing date of U.S. Provisional Application Ser. No. 60.031,338, filed Nov. 21, 1996.

BACKGROUND OF THE INVENTION

The U.S. Government has a paid-up license in this invention and the right in limited circumstances to require the patent owner to license others on reasonable terns as provided for by the terms of contract CA75979, awarded by the National Cancer Institute of the National Institutes of Health.

Throughout the application various publications are referenced in parentheses. The disclosures of these publications in their entireties are hereby incorporated by reference in the application in order to more fully describe the state of the art to which this invention pertains.

1. Field of the Invention

The present invention is related to the biomedical arts, in particular to biotechnology.

2. Discussion of the Related Art

Pituitary tumor-transforming gene (PTTG) is a recently described oncogene isolated from pituitary tumor growth hormone-secreting cells by differential display. (Pei, L., et al., *Isolation and characterization of a pituitary tumor-transforming gene (PTTG)*, Mol. Endo. 11:433–441 [1997]). PTTG is believed to be a securin protein and has 44.6% amino acid identity with Xenopus securin. (Zou, H., et al., *Identification of a vertebrate sister-chromatid separation inhibitor involved in transformation and tumorigenesis*, Science 285:418–422 [1999]; Mei, J., Huang, X., and Zhang, P., *Securin is not required for cellular viability, but is required for normal growth of mouse embryonic fibroblasts*, Current Biology 11:1197–1201 [2001]).

PTTGs have been identified in rat, mouse, and human cells. (e.g., PCT/US97/21463; Wang, Z., et al., *Pituitary tumor transforming gene (PTTG) transforming and transactivation activity*, J. Biol. Chem. 275:7459–7461 [2000]). The human PTTG family consists of at least four homologous genes, of which PTTG1 is located on chromosome 5q33. (Prezant, T. R., et al., *An intronless homolog of human proto-oncogene hPTTG is expressed in pituitary tumors: evidence for hPTTG family*, J. Clin. Endocrinol. Metab. 84:1149–1152 [1999]).

PTTG has been shown to upregulate basic fibroblast growth factor secretion (Zhang, X. et al., *Structure, expression, and function of human pituitary tumor-transforming gene (PTTG)*, Mol. Endocrinol. 13:156–66 [1999a]), and transactivate DNA transcription (Dominguez, A. et al. [1998]; Wang, Z. et al., *Pituitary tumor transforming gene (PTTG) transactivating and transforming activity*, J. Biol. Chem. 275:7459–61[2000]).

Human PTTG1 is expressed at low levels in most normal human tissues. (Chen, L. et al., *Identification of the human pituitary tumor transforming gene (hPTTG) family: molecular structure, expression, and chromosomal localization*, Gene. 248:41–50 [2000]; Heaney, A. P. et al. [2000]). PTTG is abundant only in normal testis and thymus. (Wang, Z., et al., *Characterization of the murine pituitary tumor transforming gene (PTTG) and its promoter*, Endocrinology 141:763–771 [2000]). When expressed at normal levels, PTTG mediates promoter transcriptional activation. (Wang, Z., et al., *Pituitary tumor transforming gene (PTTG) transforming and transactivation activity*, J. Biol. Chem. 275:7459–7461 [2000]). By dysregulating chromatid separation, PTTG overexpression also leads to aneuploidy, i.e., cells having one or a few chromosomes above or below the normal chromosome number (Zou et al. [1999]; Yu, R., et al., *Pituitary tumor transforming gene (PTTG) regulates placental JEG-3 cell division and survival: evidence from live cell imaging*, Mol. Endo. 14:1137–1146 [2000]). At the end of metaphase, securin is degraded by an anaphase-promoting complex, releasing tonic inhibition of separin, which in turn mediates degradation of cohesins, the proteins that hold sister chromatids together. Overexpression of a nondegradable PTTG disrupts sister chromatid separation (Zou et al. [1999]) and overexpression of PTTG causes apoptosis and inhibits mitoses (Yu, R. et al. [2000]). The securin function of PTTG suggests that PTTG may also be expressed in normal proliferating cells. In adult humans, PTTG1 mRNA is most abundant in testis, an organ containing rapidly proliferating gametes. (Zhang, X. et al. [1999a]); Wang, Z. et al. [2000]).

In contrast, PTTG1 is highly expressed in human tumors and is responsive to estrogen induction. (Zhang, X., et al., *Structure, expression, and function of human pituitary tumor-transforming gene (PTTG)*, Mol. Endo. 13:156–166 [1999a]; Heaney, A. P., et al., *Early involvement of estrogen-induced pituitary tumor transforming gene and fibroblast growth factor expression in prolactinoma pathogenesis*, Nature Med. 5:1317–1321 [1999]). Indeed, PTTG is highly expressed in pituitary tumors and neoplasms from the hematopoietic system and colon, and PTTG is considered to be a proto-oncogene, because PTTG overexpression in NIH3T3 cells induces cell transformation and in vivo tumor formation. (Pei, L., et al., *Isolation and characterization of a pituitary tumor-transforming gene (PTTG)*, Mol. Endo. 11:433–441 [1997]; Zhang, X. et al. [1999a]; Zhang, X. et al., *Pituitary tumor transforming gene (PTTG) expression in pituitary adenomas*, J. Clin. Endocrinol. Metab. 84:761–67 [1999b]; Heaney, A. P. et al., *Pituitary tumor transforming gene in colorectal tumors*, Lancet 355:712–15 [2000]; Dominguez, A. et al., *hPTTG, a human homologue of rat pttg, is overexpressed in hematopoietic neoplasms. Evidence for a transcriptional activation function of hPTTG*, Oncogene 17:2187–93 [1998]; Saez, C. et al., *hPTTG is overexpressed in pituitary adenomas and other primary epithelial neoplasias*, Oncogene 18:5473-6 [1999]). In addition, it was recently observed that PTTG1 overexpression in rat FRTL5 thyroid cells and in human thyroid cell cultures caused in vitro transformation and produces a dedifferentiated neoplastic phenotype. (Heaney, et al., *Transforming events in thyroid tumorigenesis and their association with follicular lesions*, J. Clin. Endocrinol. Metab. 86(10):5025–5032 [2001]).

The recent discovery of a human PTTG gene 2, which shares high sequence homology with human PTTG1, implying the existence of a PTTG gene family. (Prezant, T. R., et al., *An intronless homolog of human proto-oncogene hPTTG is expressed in pituitary tumors: evidence for hPTTG family*, J. Clin. Endocrinol. Metab. 84:1149–1152 [1999]). Murine PTTG shares 66% nucleotide base sequence homology with human PTTG1 and also exhibits transforming ability. (Wang, Z. and Melmed, S., *Characterization of the murine pituitary tumor transforming gone (PTTG) and its promoter*, Endocrinology [In Press; 2000]). A proline-rich region was identified near the protein C-terminus that is critical for PTTG1's transforming activity. (Zhang, X., et al. [1999a]), as demonstrated by the inhibitory effect on in vitro transformation, in vivo tumorigenesis, and transactivation, when point mutations were introduced into the proline-rich region. Proline-rich domains may function as SH3 binding sites to mediate signal transduction of protein-tyrosine kinase. (Pawson, T., *Protein modules and signaling networks*, Nature 373:573–580 [1995]; Kuriyan, J., and Cowburn, D., *Modular peptide recognition domains in eukaryotic signaling*, Annu, Rev. Biophys. Biomol. Struct. 26:259–288 [1997]).

The transforming ability of PTTG has given rise to much interest into the study of its role in tumorigenesis in various tissues and organs, including the pituitary and thyroid. Moreover, the correlation between sex steroid expression and tumorigenesis also has garnered much interest. In general, various distinct molecular events (Farid, N. R., et al., *Molecular basis of thyroid cancer*, Endocr. Rev. 15:202–232 [1994]) occurring in thyroid neoplasia, including ras mutations, detected early in both benign and malignant tumors, activation of TSH receptor, and $G_s\alpha$-subunit mutation have been reported in some follicular carcinomas. (Surez H. G., et al., *gsp mutations in human thyroid tumors*, Oncogene 6:677-679 [1991].

TSH is an important thyroid growth factor, and the cooperative regulation of thyrocyte growth by TSH and sex steriods has been supported by both animal studies and epidemiological analyses. (Clark, O. H., et al., *Estrogen and thyroid-stimulating hormone (TSH) receptors in neoplastic and nonneoplastic human thyroid tissues*, J. Surg. Res. 38:89-96 [1985]; Mori M, et al., *Effects of sex difference, gonadectomy, and estrogen on N-methyl-N-nitrosourea induced rat thyroid tumors*, Cancer Res 50(23):7662–7 [1990]).

Moreover, in addition to induction of PTTG expression in pituitary cells, estrogen administration also has been reported to increase the mean serum TSH levels in the pituitary and thyroid glands of female rats. (Mori M, et al., *Effects of sex difference, gonadectomy, and estrogen on N-methyl-N-nitrosourea induced rat thyroid tumors*, Cancer Res 50(23):7662-7 [1990]). This study also suggested a complex interplay between sex steroids and TSH on thyroid cell growth, where both male and female rats were more susceptible to radiation induced thyroid tumors in the presence of TSH stimulation, while ovariectomy or castration attenuated thyroid tumor occurrence. The complex interplay between TSH and PTTG also has been shown. That is, in a recent study, it was observed that TSH treatment of rat FRTL5 cells or primary human thyroid cells induced PTTG expression in vitro and administration of estrogen to rats induced rat thyroidal PTTG expression. (Heaney, et al., *Transforming events in thyroid tumorigenesis and their association with follicular lesions*, J. Clin. Endocrinol. Metab. 86(10):5025–5032 [2001]).

With the interest in the study of the etiology of various cancers follows the development of various treatment strategies. For example, iodine was shown to inhibit thyroid cell growth and its uptake is believed to be facilitated by sodium/iodide symporter (NIS) in thyroid follicular cells, or FRTL5 cells. Furthermore, the use of radioactive isotopes of iodine, such as $^{125}I$ and $^{131}I$ have been used to target tumor cells with high NIS gene expression.

It is also known that TSH can increase iodide uptake in a dose-dependent manner, and this effect is correlated with a rapid increase in NIS gene expression. Estradiol has been shown to block TSH-induced sodium/iodide symporter (NIS) expression, and treatment of cells with estradiol together with an estrogen receptor antagonist restored TSH-induced NIS expression to normal levels. (Furlanetto, T. W., et al., *Estradiol Increases Proliferation and Down-Regulates the Sodium/Iodide Symporter Gene in FRTL-5 Cells*1, Endocrinology 140(12): 5705–5711 [1999]; Furlanetto, T. W., et al., *Estradiol decreases iodide uptake by rat thyroid follicular FRTL-5 cells*, Braz J Med Biol Res 34(2) 259–263 [2001]). In contrast, a recent study showed that overexpression of wild-type PTTG1 in normal human thyroid cells in vitro and rat FRTL5 cells exhibited decreased $^{125}I$, uptake compared with controls. (Heaney, et al., *Transforming events in thyroid tumorigenesis and their association with follicular lesions*, J. Clin. Endocrinol. Metab. 86(10):5025–5032 [2001]).

To date, the development of an appropriate cell model for the study of the consequences of varying degrees of PTTG expression has been limited. Thus, there is a need in the art for a cellular model wherein PTTG expression, among other gene products, may be modulated and the resulting effects may be studied.

SUMMARY OF THE INVENTION

The present invention provides a thyroid stimulating hormone (TSH)-sensitive cell transfected with an expression vector comprising a DNA segment encoding a functional PTTG peptide, wherein the cell overexpresses PTTG in response to TSH. The inventive thyroid stimulating hormone (TSH)-sensitive cell is transfected with an expression vector that includes a DNA segment having a polynucleotide sequence encoding a functional PTTG peptide that has an amino acid sequence of SEQ ID NO:2, SEQ ID NO:4, or SEQ ID NO:5, an amino acid sequence that is a mutation of SEQ ID NO:2, SEQ ID NO: 4, or SEQ ID NO:5, or that encodes a functional peptide fragment of SEQ ID NO:2, SEQ ID NO:4; or SEQ ID NO:5, which fragment comprises a proline-rich region; and wherein the cell overexpresses a functional PTTG in response to TSH.

The present invention also provides an in vitro cell model for the study of genetic regulation mediated by PTTG in a mammalian cell, comprising the inventive thyroid stimulating hormone (TSH)-sensitive cell. Exposing the cell to TSH induces expression of PTTG from the expression vector.

The inventive cell model is useful in the study of the effects of PTTG expression on NIS and thyroglobulin expression. The inventive cell model can be used to modulate NIS, thyroglobulin and PTTG expression to study the physiological and/or molecular biological effects. For example, the inventive cell model can be used to study the effect of PTTG expression on iodide uptake (e.g., typically detected with $^{125}I$- or $^{131}I$-NaI) in thyroid or FRTL5 cells.

Moreover, the inventive cell model is useful in the study of the physiological and molecular biological effects of aberrant PTTG expression, PTTG over-expression, and PTTG under-expression.

The present invention is further described by the disclosures of U.S. Ser. No. 09/854,326, filed May 11, 2001, now issued as U.S. Pat. No. 6,913,926 on Jul. 5, 2005; U.S. Ser. No. 09/777,422, filed Feb. 5, 2001, now abandoned: U.S. Ser. No. 09/730,469. filed Dec. 4, 2000, now abandoned; U.S. Ser. No. 09/687,911, filed Oct. 13, 2000, now abandoned; U.S. Ser. No. 09/569,956, filed May 12, 2000, now issued as U.S. Pat. No. 6,894,031 on May 17, 2005; U.S. Ser. No. 08/894,251, filed Jul. 23, 1999, now issued as U.S. Pat. No. 6,455,305 on Sep. 24, 2002; and PCT/US97/21463 filed Nov. 21, 1997; all of which applications are incorporated herein by reference in their entireties, and by the drawings and detailed description of the preferred embodiments contained herein.

BRIEF DESCRIPTION OF THE DRAWINGS

FIG. 1 depicts PTTG expression in human thyroid tumors.

FIG. 2 depicts PTTG expression in FRTL5 cells transfected with PTTG wild type (Wt) and mutant clones.

FIG. 5 illustrates the regulation of PTTG by thyroid stimulating hormone (TSH) in vitro and estrogen (E) in vivo. FIG. 5A depicts a Northern blot illustrating PTTG expression in a primary culture of FRTL5 cells. FIG. 5B depicts a Northern blot illustrating PTTG expression in a primary culture of human thyroid cells. RNA extracted from rat testis served as a positive control. The cell cultures of both FIGS. 5A and 5B were incubated in TSH-free medium overnight before the addition of TSH (5–10 units/mL) for 24 hours. FIG. 5C depicts Northern blot analysis of thyroid tissue extracts for pttg from rats (groups of three) treated with E (1000 ng/48 hours) or E (1000 ng/48 hours) in combination with 4-hydroxytamoxifen (E+AE; 4-hydroxytamoxifen, 860 μg/48 hours) or vehicle only.

DESCRIPTION OF THE PREFERRED EMBODIMENTS OF THE INVENTION

Figure 1A:
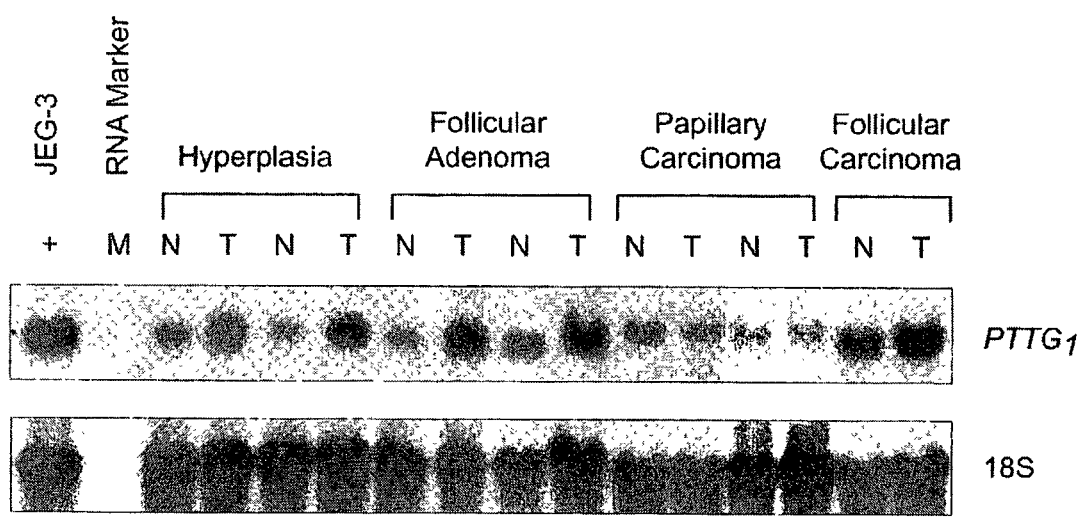
FIG. 1A illustrates a Northern blot analyses of normal (N) and thyroid tumor (T) tissue for the expression of PTTG1 mRNA. JEG-3 chorio-carcinoma cells served as a positive control. 18S ribosomal RNA served as an internal control showing uniform nucleic acid loading. Lane "M" contained molecular weight markers.

In accordance with the present invention, there are provided a thyroid stimulating hormone (TSH)-sensitive cell transfected with an expression vector comprising a DNA segment encoding functional PTTG and an in vitro cell model for the study of genetic regulation mediated by PTTG in a mammalian cell.

As used herein, the phrase "PTTG" refers to a mammalian family of isolated and/or substantially pure proteins, e.g., human (i.e., hPTTG1), that are able to transform cells in tissue culture (e.g., NIH 3T3 cells, and the like), including naturally occurring allelic variants of PTTG and variants produced via artificially induced mutations. PTTG proteins referred to herein include naturally occurring allelic variants thereof encoded by mRNA generated by alternative splicing of a primary transcript, and further include fragments which retain at least one native biological activity, such as immunogenicity.

Functional PTTG peptides referred to herein are those polypeptides specifically recognized by an anti-PTTG antibody that also specifically recognizes or binds a PTTG protein including the sequences set forth in SEQ ID NO:2, SEQ ID NO:4, and SEQ ID NO:5, and fragments of any of them that are about 5 to about 150, about 5 to about 50, about 25 to about 100, and about 50 to about 75 amino acids long, and which comprise a proline-rich region.

PTTG is further characterized by being primarily expressed in pituitary tumor cells with lower level expression detected in testis. The transcript in pituitary tumor cells is about 1.3 kb in size while the transcript in testis is about 1 kb, as observed by a Northern blot assay. Thus, splice variant cDNA transcripts encoding a PTTG family of proteins are clearly contemplated by the present invention.

In accordance with the present invention, a functional PTTG peptide contains at least one proline-rich region, which is a peptide segment having a PXXP motif, where the Xs between the proline (P) residues represent any amino acid residue, including proline. The proline-rich regions of PTTG peptides are potential SH3-binding sites. For example, in human PTTG1, proline-rich regions are found at amino acid residues 163–167 and 170–173 of SEQ ID NO:4. Likewise, in rat PTTG, there are three proline-rich regions at amino acid residues 160–163, 167–170, and 177–180 of SEQ ID NO:2. And mouse PTTG peptide comprises a proline-rich region at amino acid residues 157–160 of SEQ ID NO:5.

Thyroid Stimulating Hormone (TSH) is a hormone produced by the pituitary gland in response to signals from the hypothalamus gland. As its name suggests, TSH promotes the growth of the thyroid gland in the neck and stimulates it to produce more thyroid hormones. TSH, also known as thyrotropin, is a glycoprotein consisting of a beta chain of 112 amino acids and an alpha chain of 89 amino acids. TSH binds with membrane bound TSH receptors (TSH-R) on the cells of the thyroid gland. This receptor is not only specific for TSH, but also for TSH-R antibodies that are produced in patients with Grave's disease. The TSH-R is a transmembrane protein and uses G-protein coupled signal transduction pathways.

As used herein, a "TSH sensitive cell" is a cell that contains at least one membrane bound TSH receptor or otherwise is induced by exposure to TSH to initiate transcription of one or more genes in that cell.

Insertion (also termed "transfection") of the targeting vector into the target cells can be accomplished using a variety of methods well known in the art including for example, electroporation, microparticle bombardment, microinjection, viral transduction, and calcium phosphate treatment (see Lovell-Badge, in Robertson, ed., supra). Another useful in vitro method of insertion is electroporation.

The PTTG-containing vector to be transfected into the cells can first be linearized if the PTTG gene has previously been inserted into a circular vector. Linearization can be accomplished by digesting the DNA with a suitable restriction endonuclease selected to cut only within the vector sequence and not within the inserted PTTG sequence.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome. In addition, vectors may contain appropriate packaging signals that enable the vector to be packaged by a number of viral virions, e.g., retroviruses, herpes viruses, adenoviruses, resulting in the formation of a "viral vector."

If the cells are to be electroporated, the cells and vector DNA are exposed to an electric pulse using an electroporation machine and following the manufacturer's guidelines for use. After electroporation, the cells are typically allowed to recover under suitable incubation conditions. The cells are then screened for the presence of the targeting vector.

Screening the transfected cells can be accomplished using a variety of methods, but typically, one screens for the presence of the selectable marker sequence portion of the vector. Where the selectable marker sequence is an antibiotic resistance gene, the cells can be cultured in the presence of an otherwise lethal concentration of antibiotic. Those cells that survive have presumably integrated the targeting vector. If the selectable marker sequence is other than an antibiotic resistance gene, a Southern blot of the cell genomic DNA can be probed with a sequence of DNA designed to hybridize only to the marker sequence. If the selectable marker sequence is a gene that encodes an enzyme whose activity can be detected (e.g., beta-galactosidase), the enzyme substrate can be added to the cells under suitable conditions, and the enzymatic activity of the selectable marker sequence can be analyzed.

Use of the terms "isolated" and/or "purified" in the present specification and claims as a modifier of DNA, RNA, polypeptide or proteins means that the DNA, RNA, polypeptide or proteins so designated have been produced in such form by the hand of man, and thus are separated from their native in vivo cellular environment. As a result of this human intervention, the recombinant DNAs, RNAs, polypeptide and proteins of the invention are useful in ways described herein that the DNAs, RNAs, polypeptide or proteins as they naturally occur are not.

As used herein, the term "mammal" or "mammalian" refers to warm-blooded vertebrate animals belonging to the class mammalia, including all that possess hair and suckle their young, e.g., human, rat, mouse, rabbit, monkey, baboon, bovine, porcine, ovine, canine, feline, and the like. As used herein, "mammalian cell" refers to a somatic or germ line cell in vitro or in an in vivo whole animal. Such a cell can be derived, harvested, isolated selected, removed, extracted, or otherwise obtained from a mammal by any means.

PTTG is the gene, which is responsible for pituitary tumorigenesis. A search of GenBank and protein profile analysis (BLAST Program search of databases of the national center for Biotechnology Information) indicated that PTTG shares no homology with known sequences, and its encoded protein is highly hydrophilic.

Presently preferred PTTG proteins include amino acid sequences that are substantially the same as the amino acid sequence SEQ ID NO:2, SEQ ID NO:4, or SEQ ID NO:5, and fragments thereof as described above, as well as biologically active, modified forms thereof. Those of skill in the art will recognize that numerous residues of the above-described sequences can be substituted with other, chemically, sterically and/or electronically similar residues without substantially altering the biological activity of the resulting receptor species. In addition, larger polypeptide sequences containing substantially the same sequence as SEQ ID NO:2 SEQ ID NO:4, or SEQ ID NO:5 therein (e.g., splice variants) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence;

with greater than about 95% amino acid sequence identity being especially preferred. It is recognized, however, that polypeptide (or nucleic acids referred to hereinbefore) containing less than the described levels of sequence identity arising as splice variants or that are modified by conservative amino acid substitutions, or by substitution of degenerate codons are also encompassed within the scope of the present invention.

For purposes of the present invention, the term "biologically active" or "functional", when used herein as a modifier of a full-length PTTG protein, or polypeptide fragment thereof, refers to a peptide that exhibits at least one of the functional characteristics attributed to PTTG. For example, one biological activity of PTTG is the ability to transform cells in vitro (e.g., NIH 3T3 cells, and the like). Another function or biological activity of PTTG is the ability to induce tumor formation in nude mice (e.g., when transfected into NIH 3T3 cells, and the like). Another biological activity is the ability to modulate the activation of mammalian T-lymphocytes. Another biological activity of PTTG is the ability to inhibit separin activity in the nucleus during mitosis. Yet another function or biological activity of PTTG is the feature of having its expression induced or stimulated in response to TSH or estrogen.

An example of the means for preparing the inventive peptide(s) is to express nucleic acids encoding the PTTG in a suitable host cell using known recombinant DNA technology, such as in a bacterial cell, a yeast cell, an amphibian cell (i.e., oocyte), or a mammalian cell, using methods well known in the art, and recovering the expressed polypeptide, again using well-known methods. The PTTG polypeptide of the invention may be isolated directly from cells that have been transformed with expression vectors as described herein. The inventive polypeptide, biologically active fragments, and functional equivalents thereof can also be produced by chemical synthesis. For example, synthetic polypeptide can be produced using Applied Biosystems, Inc. Model 430A or 431A automatic peptide synthesizer (Foster City, Calif.) employing the chemistry provided by the manufacturer.

As used herein, expression or to express refers to the process by which polynucleic acids are transcribed into mRNA and translated into peptides, polypeptide, or proteins. If the polynucleic acid is derived from genomic DNA, expression may, if an appropriate eukaryotic host cell or organism is selected, include splicing of the mRNA.

Also encompassed by the term PTTG are polypeptide fragments or polypeptide analogs thereof. The term "polypeptide analog" includes any polypeptide having an amino acid residue sequence substantially identical to a sequence specifically shown herein in which one or more residues have been conservatively substituted with a functionally similar residue and which displays the ability to mimic PTTG as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue, provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptide of the present invention also include any polypeptide having one or more additions and/or deletions of residues, relative to the sequence of a polypeptide whose sequence is shown herein, so long as the requisite activity is maintained.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a PTTG protein. One means of isolating a nucleic acid encoding an PTTG polypeptide is to probe a mammalian genomic library with a natural or artificially designed DNA probe using methods well known in the art. DNA probes derived from the PTTG gene are particularly useful for this purpose. DNA and cDNA molecules that encode PTTG polypeptide can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an PTTG polypeptide. Such nucleic acids may include, but are not limited to, nucleic acids comprising SEQ ID NO:1, SEQ ID NO: 3, or SEQ ID NO:6, alleles thereof, preferably at least nucleotides 293–889 of SEQ ID NO:1 (coding sequence for full-length rat PTTG), at least nucleotides 95–700 of SEQ ID NO:3 (i.e., coding sequence for full-length human PTTG1), or at least nucleotides 304–891 of SEQ ID NO:6 (i.e., coding sequence for full-length mouse PTTG), or splice variant cDNA sequences thereof.

As used herein, the phrases "splice variant" or "alternatively spliced", when used to describe a particular nucleotide sequence encoding an invention receptor, refers to a cDNA sequence that results from the well known eukaryotic RNA splicing process. The RNA splicing process involves the removal of introns and the joining of exons from eukaryotic primary RNA transcripts to create mature RNA molecules of the cytoplasm. Methods of isolating splice variant nucleotide sequences are well known in the art. For example, one of skill in the art may employ nucleotide probes derived from the PTTG-encoding DNA of SEQ ID NO:1, SEQ. ID NO: 3, or SEQ ID NO:6, alleles thereof, splice variants thereof or fragments thereof about 10 to about 150, about 25 to about 75, or about 50 to about 100 nucleotides long and their anti-sense nucleic acids to screen the cDNA or genomic library of the same or other species as described herein.

In one embodiment of the present invention, DNAs encoding the PTTG proteins of this invention comprise SEQ. ID NO:1, SEQ. ID No: 3, or SEQ ID NO:6, alleles thereof, splice variants thereof and fragments thereof about 15 to about 150, about 25 to about 75, or about 50 to about 100 nucleotides long and anti-sense nucleic acids thereof. In another embodiment of the present invention, DNA molecules encoding the invention proteins comprise nucleotides 293–889 of SEQ ID NO:1, alleles thereof, splice variants thereof and fragments thereof about 10 to about 150, about 25 to about 75, or about 50 to about 100 nucleotides long. In yet another embodiment, the DNA comprises nucleotides 95–700 of SEQ ID NO:3, alleles thereof, splice variants thereof and fragments thereof about 10 to about 150, about 25 to about 75, or about 50 to about 100 nucleotides long. In yet another embodiment, the DNA comprises nucleotides 304–891 of SEQ ID NO:6 of SEQ ID NO:3, alleles thereof, splice variants thereof and fragments thereof about 10 to about 150, about 25 to about 75, or about 50 to about 100 nucleotides long.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2, SEQ ID NO:4, SEQ ID NO:5, or a larger amino acid sequences including SEQ ID NO:2, SEQ ID NO:4, or SEQ ID NO:5. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

The present invention also encompasses nucleic acids which differ from the nucleic acids shown in SEQ ID NO:1, SEQ ID NO:3, or SEQ ID NO:6, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptide that are the same as those disclosed herein or that have conservative amino acid variations, or that encode larger polypeptides that include SEQ ID NO:2, SEQ ID NO:4, or SEQ ID NO:5. For example, conservative variations include substitution of a non-polar residue with another non-polar residue, or substitution of a charged residue with a similarly charged residue. These variations include those recognized by skilled artisans as those that do not substantially alter the tertiary structure of the protein.

Nucleic acids encoding PTTG polypeptides, by virtue of the degeneracy of the genetic code, do not necessarily hybridize to the nucleic acids set forth in SEQ ID NO:1, SEQ. ID No: 3, and/or SEQ ID NO:6 under specified hybridization conditions. Preferred nucleic acids encoding the PTTG polypeptide of the invention comprise nucleotides encoding SEQ ID NO:1, SEQ. ID No: 3, SEQ ID NO:6, and fragments thereof about 5 to about 150, about 5 to about 50, about 25 to about 75, or about 50 to about 100 amino acids long. Exemplary nucleic acids encoding a PTTG protein of the invention may be selected from the following.

(a) DNA encoding the amino acid sequence set forth in SEQ. ID NO:2, SEQ. ID No: 4, or SEQ ID NO:5,
(b) DNA that hybridizes to the DNA of (a) under moderately stringent conditions, wherein said DNA encodes biologically active PTTG, or
(c) DNA degenerate with respect to either (a) or (b) above, wherein said DNA encodes biologically active PTTG.

Hybridization refers to the binding of complementary strands of nucleic acid (i.e., sense:antisense strands or probe: target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42EC, followed by washing in 0.2×SSPE, 0.2% SDS, at 65EC.

The phrase "high stringency hybridization" refers to conditions that permit hybridization of only those nucleic acid sequences that form stable hybrids in 0.018 M NaCl at 65EC (i.e., if a hybrid is not stable in 0.018 M NaCl at 65EC, it will not be stable under high stringency conditions, as contemplated herein). High stringency conditions can be provided, for example, by hybridization in 50% formamide, 5×Denhart's solution, 5×SSPE, 0.2% SDS at 42EC, followed by washing in 0.1×SSPE, and 0.1% SDS at 65EC.

The phrase "low stringency hybridization" refers to conditions equivalent to hybridization in 10% formamide, 5×Denhart's solution, 6×SSPE, 0.2% SDS at 42EC, followed by washing in 1×SSPE, 0.2% SDS, at 50EC. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1, SEQ ID NO:3, or SEQ ID NO:6, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions, i.e., typically at least 15–30 nucleotide, of SEQ ID NO:1, SEQ. ID No: 3, or of SEQ ID NO:6, although longer fragments are also contemplated.

Mutant PTTG cDNAs can be produced by a variety of methods well-known in the art, including deletions and site-directed mutagenesis of any region of PTTG cDNA. For example, mutations can be introduced by overlap extension PCR (A. Aiyar et al., Methods Mol. Biol. 57:177-91 [1996]) with Pfu polymerase and 5% DMSO, by using an external sense primer and antisense primer. Internal mutagenizing primers can be used to cause deletions of specific nucleotides. Gel-purified PCR-products and the original template can then be digested with appropriate restriction endonucleases, the resulting fragments purified, and the mutated fragments re-ligated into the vector for transfection. For site-directed mutagenesis, the Transformer Mutagenesis Kit (available from Clontech) can be used to construct a variety of missense and/or nonsense mutations to PTTG cDNA. The skilled practitioner is aware of suitable methods for site-directed mutagenesis, e.g., the method of Deng and Nickoloff (W. P. Deng and J. A. Nickoloff, Analyt. Biochem.200: 81–88 [1992]), and commercial site-directed mutagenesis kits are available, for example the Transformer® site-directed mutagenesis kit (Clontech).

The invention nucleic acids can be produced by a variety of methods well-known in the art, e.g., the methods described herein, employing PCR amplification using oligonucleotide primers from suitable regions of SEQ ID NO:1 or SEQ ID NO:3, or SEQ ID NO:6, and the like.

In accordance with the present invention, optionally labeled PTTG-encoding cDNAs, or fragments thereof, can be employed to probe library(ies) (e.g., cDNA, genomic, and the like) for additional nucleic acid sequences encoding related novel mammalian PTTG proteins. Construction of mammalian cDNA and genomic libraries, preferably a human library, is well-known in the art. Screening of such a cDNA or genomic library is initially carried out under low-stringency conditions, which comprise a temperature of less than about 42EC, a formamide concentration of less than about 50%, and a moderate to low salt concentration.

Probe-based screening conditions can comprise a temperature of about 37° C., a formamide concentration of about 20%, and a salt concentration of about 5×standard saline citrate (SSC; 20×SSC contains 3 M sodium chloride, 0.3 M sodium citrate, pH 7.0). Such conditions will allow the identification of sequences which have a substantial degree of similarity with the probe sequence, without requiring perfect homology. The phrase "substantial similarity" refers to sequences which share at least 50% homology. In some instances, hybridization conditions will be selected which allow the identification of sequences having at least 70% homology with the probe, while discriminating against sequences which have a lower degree of homology with the probe. As a result, nucleic acids having substantially the same, i.e., similar, sequence as the coding region of the nucleic acids of the invention, preferably as nucleotides 293–889 of SEQ ID NO:, nucleotides 95–700 of SEQ ID NO:3, or 304–891 of SEQ ID NO:6 are obtained.

Such nucleic acids may include, but are not limited to, nucleic acids comprising SEQ ID NO:1, SEQ ID NO: 3, or SEQ ID NO:6, alleles thereof, preferably at least nucleotides 293–889 of SEQ ID NO:1, at least nucleotides 95–700 of SEQ ID NO:3, or at least nucleotides 304–891 of SEQ ID NO:6, or splice variant cDNA sequences thereof.

As used herein, a nucleic acid "probe" is single-stranded DNA or RNA, or analogs thereof, that has a sequence of nucleotide that includes at least 14, preferably at least 20, more preferably at least 50, contiguous bases that are the same as (or the complement of) any 14 or more contiguous bases set forth in any of SEQ ID NO: 1, SEQ. ID NO: 3, or SEQ ID NO:6. Preferred regions from which to construct probes include 5' and/or 3' coding regions of SEQ ID NO:1 SEQ. ID NO: 3, or SEQ ID NO:6. In addition, the entire cDNA encoding region of an invention PTTG protein, or the entire sequence corresponding to SEQ ID NO:1, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in Antibody As a Tool, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptide, and proteins, is well known in the art. For instance, an invention antibody can be labeled by metabolic incorporation of radiolabeled amino acids provided in the culture medium. See, for example, Galfre et al., Meth. Enzymol., 7 3:3–46 (1981). Conventional means of protein conjugation or coupling by activated functional groups are particularly applicable. See, for example, Aurameas et al., Scand. J. Immunol., Vol. 8, Suppl. 7:7–23 (1978), Rodwell et al., Biotech., 3:889–894 (1984), and U.S. Pat. No. 4,493, 795.

The present invention provides means to modulate levels of expression of PTTG polypeptide in a TSH-sensitive cell transfected with an expression vector comprising a DNA segment encoding functional PTTG. As used herein, the term "modulate" means to adjust or vary the expression of a particular polynucleotide, which codes for a particular polypeptide, in a cell by subjecting said cell or cells to a stimulus For example, PTTG expression in a TSH-sensitive cell can be modulated by subjecting said cell to TSH.

In accordance with yet another embodiment of the present invention, there is provided a method for the recombinant production of invention PTTG protein(s) by expressing the above-described nucleic acid sequences in suitable host cells. Recombinant DNA expression systems that are suitable to produce PTTG proteins described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include promoters that induce overexpression of PTTG in response to TSH or estrogen induction, such as human PTTG1, rat PTTG, or mouse PTTG promoters, and the like.

As used herein, the terms "overexpress" and "overexpression" refer to expression of a particular nucleic acid in a specific cell-type at a level that exceeds the level at which the nucleic acid typically is expressed in wild-type cells of that specific cell-type. As used herein, the terms "underexpress" and "underexpression" refer to expression of a particular nucleic acid in a specific cell-type at a level that is lower than the level at which the nucleic acid typically is expressed in wild-type cells of that specific cell-type.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

Prokaryotic transformation vectors are well-known in the art and include pCiNeo, and the like.

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg, 1979, Nature Vol. 277:108–114) the Okayama-Berg cloning system (*Mol. Cell Biol.* Vol. 2:161–170, 1982), and the expression cloning vector described by Genetics Institute (*Science* Vol. 228:810–815, 1985), are available which provide substantial assurance of at least some expression of the protein of interest in the transformed eukaryotic cell line.

Particularly preferred base vectors contain regulatory elements that can be linked to the invention PTTG-encoding DNAs for transfection of mammalian cells, such that positive trasnfectants can be identified or detected by means known in the art.

In accordance with another embodiment of the present invention, there are provided "recombinant cells" containing the nucleic acid molecules (i.e., DNA or mRNA) of the present invention. Methods of transforming suitable host cells, preferably FRTL5 cells, as well as methods applicable for culturing said cells are generally known in the art. See, for example, Sambrook et al., *Molecular Cloning: A Laboratory Manual* (2 ed.), Cold Spring Harbor Laboratory Press, Cold Spring Harbor, N.Y., USA (1989).

Exemplary methods of introducing (transducing) expression vectors containing invention nucleic acids into host cells to produce transduced recombinant cells (i.e., cells containing recombinant heterologous nucleic acid) are well-known in the art (see, for review, Friedmann, 1989, *Science*, 244:1275–1281; Mulligan, 1993, *Science*, 260:926–932, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extrachromosomal (i.e., episomal) maintenance, or the heterologous DNA can be caused to integrate into the genome of the host (as an alternative means to ensure stable maintenance in the host).

Host organisms contemplated for use in the practice of the present invention include those organisms in which recombinant production of proteins coded for by the transfected polynucleotide has been carried out. Examples of such host organisms include mammalian cells (e.g., FRTL5 cells), and the like. Presently preferred host organisms are mammalian thyroid stimulating hormone-sensitive or estrogen-sensitive cells.

In accordance with another embodiment of the present invention, transformed host cells that recombinantly express invention PTTG polypeptide can be contacted with a test compound, and the modulating effect(s) thereof can then be evaluated by comparing the PTTG-mediated response (e.g., via reporter gene expression) in the presence and absence of test compound, or by comparing the response of test cells or control cells (i.e., cells that do not express PTTG polypeptide), to the presence of the compound.

As used herein, a compound or a signal that "modulates the activity" of invention PTTG polypeptide refers to a compound or a signal that alters the activity of PTTG polypeptide so that the activity of the invention PTTG polypeptide is different in the presence of the compound or signal than in the absence of the compound or signal. In particular, such compounds or signals include agonists and antagonists. An agonist encompasses a compound or a signal that activates PTTG protein function. Agonists include estrogen and TSH. Alternatively, an antagonist includes a compound or signal that interferes with PTTG protein function. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate PTTG activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of PTTG polypeptide can be modulated by contacting the polypeptide with an effective amount of at least one compound identified by the above-described bioassays.

All US patents and all publications mentioned herein are incorporated in their entirety by reference thereto. The invention will now be described in greater detail by reference to the following non-limiting examples.

Unless otherwise stated, the present invention was performed using standard procedures, as described, for example in *Maniatis et al., Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987).

EXAMPLES

Example 1

Materials and Methods

Patients and Tissues. Samples of thyroid tumors (thyroid hyperplasia, n=15; follicular adenoma, n=9; follicular carcinoma, n=2; papillary carcinoma, n=8; Hashimoto's disease, n=3; Table 1) were obtained from 46 consecutive unselected patients after surgical resection. Nondegraded RNA of suitable quality was obtained from 37 of the 46 tissue samples and used for further analysis. Normal adjacent thyroid tissue was obtained from 29 of the 37 analyzed cases with thyroid tumors, and postmortem normal thyroid tissue was obtained from an additional 5 cases (Brain and Tissue Banks for Developmental Disorders, University of Maryland, Baltimore, Md.). Sample aliquots were either immersed in liquid nitrogen and stored at −70° C. or fixed in 10% formalin until analysis.

TABLE 1

Patient demographics, histological diagnosis, and $PTTG_1$ expression in 37 thyroid tumors in comparison to $PTTG_1$ expression in normal thyroid tissue.

| Patient No. | Sex | Age (yr) | Diagnosis | $PTTG_1$ fold increase |
|---|---|---|---|---|
| | F | 65 | Nodular hyperplasia | 0.3 |
| | F | 44 | Nodular hyperplasia | 0.31 |
| | M | 32 | Nodular hyperplasia | 0.38 |
| | M | 41 | Nodular hyperplasia | 0.56 |
| | F | 54 | Nodular hyperplasia | 0.84 |
| | F | 69 | Nodular hyperplasia | 1.06 |
| | M | 46 | Nodular hyperplasia | 1.11 |
| | F | 32 | Nodular hyperplasia | 1.16 |
| | M | 63 | Nodular hyperplasia | 1.28 |
| | F | 59 | Nodular hyperplasia | 1.52 |
| | F | 52 | Nodular hyperplasia | 1.66 |
| | F | 40 | Nodular hyperplasia | 1.84 |
| | F | 50 | Nodular hyperplasia | 2.38 |
| | M | 57 | Nodular hyperplasia | 4.26 |
| | F | 46 | Nodular hyperplasia | 7.23 |
| Mean ± SEM | | | | 1.7(0.5) |
| | F | 88 | Follicular adenoma | 0.89 |
| | M | 32 | Follicular adenoma | 0.97 |
| | F | 42 | Follicular adenoma | 1.22 |
| | M | 36 | Follicular adenoma | 1.27 |
| | F | 24 | Follicular adenoma | 1.83 |
| | F | 60 | Follicular adenoma | 2.06 |
| | M | 53 | Follicular adenoma | 2.32 |
| | F | 62 | Follicular adenoma | 3.17 |
| | F | 57 | Follicular adenoma | 3.22 |
| Mean ± SEM | | | | 1.9(0.3) |
| | M | 71 | Follicular carcinoma | 1.4 |
| | F | 42 | Follicular carcinoma | 2.65 |
| Mean ± SEM | | | | 2.0(0.6) |
| | F | 37 | Papillary carcinoma | 0.33 |
| | F | 44 | Papillary carcinoma | 0.33 |
| 19. | M | 76 | Papillary carcinoma | 0.53 |
| 30. | M | 34 | Papillary carcinoma | 0.75 |
| | F | 47 | Papillary carcinoma | 1.08 |
| | F | 21 | Papillary carcinoma | 1.10 |
| | F | 64 | Papillary carcinoma | 1.19 |
| | F | 51 | Papillary carcinoma | 1.19 |
| Mean ± SEM | | | | 0.8(0.1) |
| 36. | F | 28 | Hashimoto's thyroiditis | 0.85 |
| 36. | F | 46 | Hashimoto's thyroiditis | 0.89 |
| 37. | M | 38 | Hashimoto's thyroiditis | 0.97 |
| Mean ± SEM | | | | 0.9(0.1) |

Northern blot analysis. Total RNA was extracted from cell cultures (about $3 \times 10^7$ cells/group) and excised tissues (after tissue homogenization) with TRIzol (Life Technologies, Inc., Gaithersburg, Md.). RNA derived from JEG3 choriocarcinoma cells or rat testis served as a positive control for PTTG1 expression. Electrophoresed RNA was transferred to Hybond-N nylon membranes (Amersham International, Little Chalfont, UK). The membrane was cross-linked, prehybridized (1 hour), and hybridized (2 hours) at 68° C. with human PTTG cDNA in the presence of 100 μg/ml salmon sperm DNA (Stratagene, La Jolla, Calif.). A 900-bp human $PTTG_1$ cDNA fragment spanning the entire coding region was labeled with [$\alpha$-$^{32}$P]deoxy-CTP using Klenow enzyme (Life Technologies, Inc.). Sodium iodide symporter (NIS) cDNA was a gift from Nancy Carrasco (Albert Einstein College of Medicine, New York, N.Y.). Posthybridization washes were followed by air-drying and autoradiography. $PTTG_1$ mRNA expression was quantitated using scanning densitometry, normalized to 18S rRNA expression, and expressed as the fold increase compared with $PTTG_1$/18S rRNA ratios in either adjacent normal thyroid tissue (29 of 37) or the mean $PTTG_1$/18S rRNA ratio measured in 32 normal thyroid tissues (mean±2 SD). The mean±SEM $PTTG_1$/18S rRNA ratio in normal thyroid tissue was 0.56±0.04 arbitrary units.

Western blot analysis. Proteins were prepared from thyroid tissues and cells using RIPA buffer (100 mM NaCl, 0.1% Triton X-100, and 50 mM Tris, pH 8.3) containing a cocktail of enzyme inhibitors (1 mM phenylmethylsulfonylfluoride, 2 μg/ml aprotinin, and 200 μg/ml leupeptin) and denatured (2 min, 100° C.) in loading buffer. The protein concentration was determined by the Bradford assay using BSA as a standard. Soluble proteins (50 μg) were separated by electrophoresis in 12% SDS-PAGE gels, transferred to polyvinylidene difluoride membranes (Amersham Pharmacia Biotech), and incubated in 5% nonfat milk in PBS-0.05% Tween solution, followed by incubation with antibodies to PTTG (1:5000) for 24 hours at 4° C. or with proliferating cytoplasmic nuclear antigen (PCNA) for 2 hours at room temperature. After washing in PBS-0.05% Tween (six times, 10 min each time), blots were incubated with appropriate horseradish peroxidase-conjugated anti-IgGs for 1 hour at room temperature. After further washes, antigen-antibody complexes were visualized by the ECL chemiluminescence detection system on Hyperfilm ECL (Amersham International).

Statistical analysis. Results are expressed as the mean±*SEM*, and statistical analysis was performed using ANOVA (Bonferroni's multiple comparison test), taking $P<0.05$ as significant.

Cell culture. Rat FRTL5 cells (American Type Culture Collection, Manassas, Va.) were maintained in Coon's modified F-12 (Life Technologies, Inc.) supplemented with antibiotics (such as penicillin, streptomycin, and fungazone), 5% calf serum, and six growth factors as previously described. (Ambesi-Impombiato, F. S., et al., *Thyroid cells in culture*, Int. Rev. Cytol. 10:163–172 [1979]). TSH was omitted overnight before TSH induction studies. For primary thyroid cultures, normal thyroid tissue obtained at surgery was minced mechanically and digested for 3 hours at 37° C. with 10 mg collagenase, 1 mg hyaluronidase, and 1 mg deoxyribonuclease I (Sigma, St. Louis, Mo.) in 10 ml F-12 medium. Cells were then cultured for 48 hours in Coon's modified medium as described above for 24 hours before transient transfection studies (below).

Cell transfection. FRTL-5 cells were transfected with wild-type (Wt) and mutant human PTTG cDNA (Zhang, X, et al., *Structure, expression and function of human pituitary transforming gene (PTTG)*, Mol. Endocrinol. 13:156–166 [1999]) subcloned in-frame into the mammalian expression vector pCiNeo (Promega Corp., Madison, Wis.) using Effectene (QIA-GEN, Chatsworth, Calif.), and transfected cells were selected and maintained in medium supplemented with G418 (Geneticin, Life Technologies, Inc.; 1 mg/mL), before screening for mRNA and protein expression. FRTL5 cells transfected with the original pCiNeo vector served as controls, and all experiments were carried out within 20 passages to minimize aging effects in the FRTL5 cells. Primary thyroid cells cultures were transiently transfected using Effectene (QIAGEN, Stanford, Valencia, Calif.), 48 hours after initial culture with Wt-PTTG or vector alone, along with a PSVβ-galactosidase expression vector. Measurement of β-galactosidase expression confirmed equivalent transfection efficiency in vector- and Wt-PTTG transfectants.

PTTG transformation in vitro. For soft agar assay, 60-mm tissue culture plates were coated with 5 ml soft agar (20% 2×F-12, 50% F-12, 10% FBS, and 20% 2.5% agar). Two milliliters of cells suspended in medium were combined with 4 ml agar mixture, and 1.5 ml were added to each plate. Cells were plated ($10^4$/dish) and incubated for 14 d, and the number of large colonies (>20 cells) was counted.

Cell proliferation assay. Cell proliferation was measured using CellTiter 96 3-[4,5-dimethylthiazol-2-yl]-2,5-diphenyltetrazolium bromide nonradioactive cell proliferation assay according to the manufacturer's protocol (Promega Corp.). This is a colorimetric assay to determine the number of viable cells based on the cellular conversion of a tetrazolium salt into medium soluble formazan. Absorbance at 14 nm is directly proportional to the number of living cells in culture. Cells (n=5000) were seeded in 96-well plates (8 wells for each clone in each assay) and incubated at 37° C. for 24–72 hours. At each time point, dye (20 µL) was added to the wells, and after further incubation at 37° C. (4 hours), absorbance was recorded at 490 nm using an ELISA reader.

Immunocytochemistry. Cells cultured on microscope slides in 100 mm plates were fixed in 4% paraformaldehyde, incubated with monoclonal antibody to PCNA (clone PC10, DAKO Corp., Carpinteria, Calif.), followed by biotinylated secondary antibodies and streptavidinhorseradish peroxidase. Antibody localization was effected using 3,3'-diaminobenzidene tetrachloride. Appropriate positive and negative controls were included.

Assays of iodide uptake. $^{125}$I-iodide uptake was measured as previously described with minor modifications. (Weiss, S. J., et al., *Iodide transport in a continuous line of cultured ells from rat thyroid*, Endocrinology 114:1090–1098 [1984]). FRTL5 cells (2×105) were seeded into 24-well tissue culture plates (Costar, Cambridge, Mass.). Twenty-four hours after transfection with Wt-PTTG or vector control (primary human thyroid cultures; n=3) or 2–3 days after plating (FRTL5 cells), culture medium was aspirated, and cells were washed with 1 ml HBSS. Iodide uptake was initiated by adding 500 µl HBSS containing 0.1 µCi carrier-free [$^{125}$I]-NaI and 10 µm/liter sodium iodide for 60 min at 37° C. The assays were terminated by aspiration of radioactive medium and washing with 1 mL ice-cold HBSS; 1.0 ml 95% ethanol was added to each well for 1 hour and then transferred to vials before counting in a γ-counter. The DNA content in each well was measured, and results were expressed as counts per min/µg DNA. All experiments were performed multiple times (8 wells for each FRTL5 clone and 3 wells for primary human thyroid cultures) on 2 separate occasions.

Animals. Ovariectomized Fischer 344 rats (140–150 g; Harlan Sprague Dawley, Inc., Indianapolis, Ind.) were housed in a controlled environment (lights on, 0600–1800 hours; 22±1° C.) with free access to food and water. The use of rats was approved by the institutional animal care and use committee. Subcutaneously implanted osmotic pumps (100 µL; Alzet, Palo Alto, Calif.), containing 17β-Estrogen-2 (1–1000 ng) or 4-hydroxytamoxifen (860 µg) in 90% polyethylene glycol/10% ethanol solution were employed to administer estrogen and/or anti-estrogen. (Heaney, A. P., et al., *Early involvement of estrogen-induced pituitary tumor transforming gene (PTTG1) and fibroblast growth factor (bFGF) expression in prolactinoma pathogenesis*, Nat. Med. 5:1317–1321 [1999]). Rats were euthanized by $CO_2$ inhalation, thyroid tissues were immersed in liquid $N_2$ and stored at −80° C. for RNA and/or protein extraction, and serum was collected for estrogen-2 and progesterone assays. (Lapolt, P. S., et al., *The relation of ovarian steroid levels in young female rats to subsequent estrous cyclicity and reproductive function during aging*, Biol. Reprod. 35:1131–1139 [1986].)

Example 2

Results

PTTG over-expression is Associated with Follicular Lesions

Figure 1B:
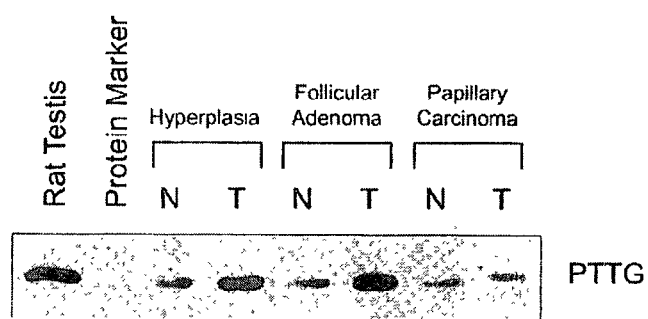
FIG. 1B shows a Western (B) blot analyses of normal (N) and thyroid tumor (T) tissue for the expression of PTTG1 protein. An extract from rat testis served as a positive control.

Increased PTTG1 mRNA expression was observed in 10 of 15 cases of thyroid hyperplasia (mean±SEM: PTTG1, mRNA, 1.7±0.5-fold increase; P<0.01, by ANOVA), 7 of 9 follicular adenomas (PTTG1 mRNA, 1.9±0.9-fold increase; P<0.01), 2 of 2 minimally invasive follicular carcinomas (PTTG1 mRNA, 2.0±0.4-fold increase). Modest PTTG increase was noted in 4 of 8 papillary carcinomas (PTTG1 mRNA, 0.84±0.15-fold increase; P=NS; Table 1 and FIG. 1A and FIG. 1B) compared to mean±2 SD PTTG1 mRNA expression in 32 normal thyroid tissues. The highest expression (up to 7.2 PTTG1, mRNA fold increase) was observed in a subset of thyroid hyperplasia, follicular adenomas, and the 2 follicular carcinomas examined (Table 1). PTTG1, mRNA expression in 3 of 3 cases of Hashimoto's disease was similar to that observed in normal thyroid tissue.

PTTG Induces Thyroid Cellular Transformation in vitro

It is known that PTTG contains a proline-rich region containing a PXXP motif near the C-terminus of the PTTG protein. (Farid N. R., et al., *Molecular basis of thyroid cancer*, Endocr. Rev. 15:202–232 [1994]). The importance of this potential SH3-binding motif in PTTG-mediated actions previously was described and it was shown that mutation of this proline-rich (P163A, P170L, P172A, P173L) motif abrogates PTTG-mediated cellular actions (Farid N. R., et al., *Molecular basis of thyroid cancer*, Endocr. Rev. 15:202–232 [1994]). To explore the role of PTTG in thyroid tumorigenesis, mutant and wild-type PTTG cDNA cloned into a mammalian expression vector under the control of the cytomegalovirus promoter were stably transfected into rat FRTL5 cells.

Figure 2A:
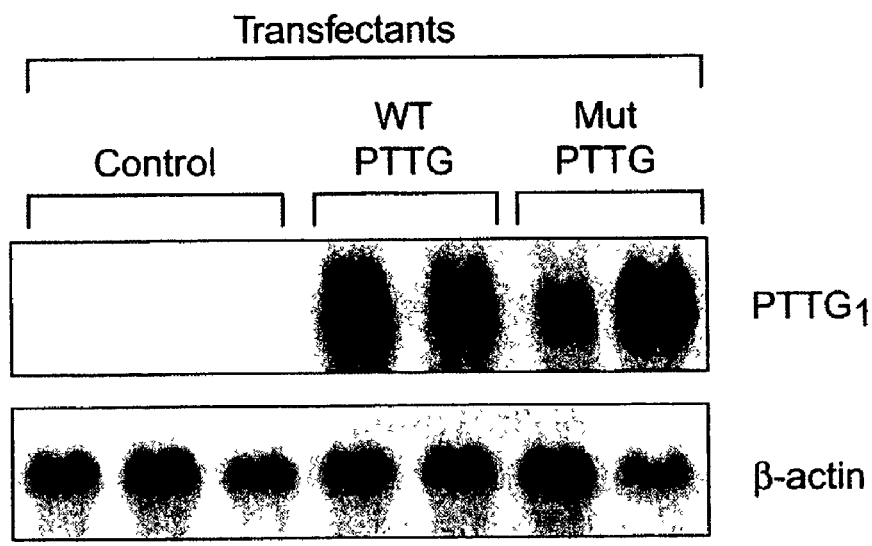
FIG. 2A depicts a representative Northern blot showing PTTG1 mRNA expression in tranfected clonal cell lines. β-actin mRNA served to show uniform loading.
Figure 2B:
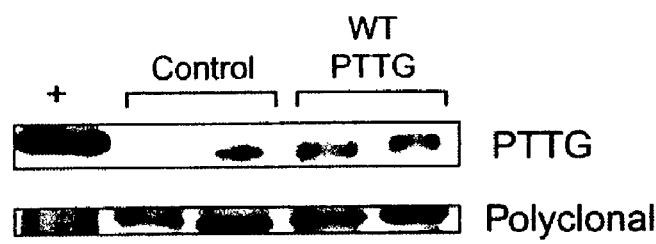
FIG. 2B depicts a representative Western blot showing PTTG1 protein expression in clonal cell lines. Positive control ("+") was an extract of rat testis. The panel marked "Polyclonal" represents an internal control.
Figure 2C:
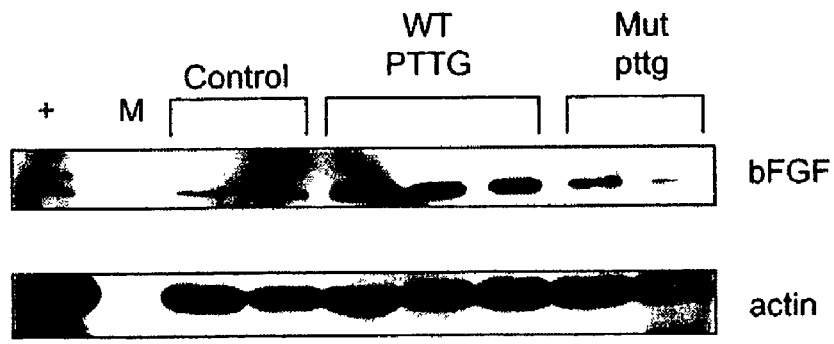
FIG. 2C depicts a representative Western blot showing increased basic fibroblast growth factor (bFGF) expression in Wt-PTTG transfectants as compared with vector- and mutant-PTTG transfectants. Positive control ("+") was an extract of rat aorta. "M" indicates molecular weight markers. Expression of β-actin protein was used as an internal control.
Figure 2D:
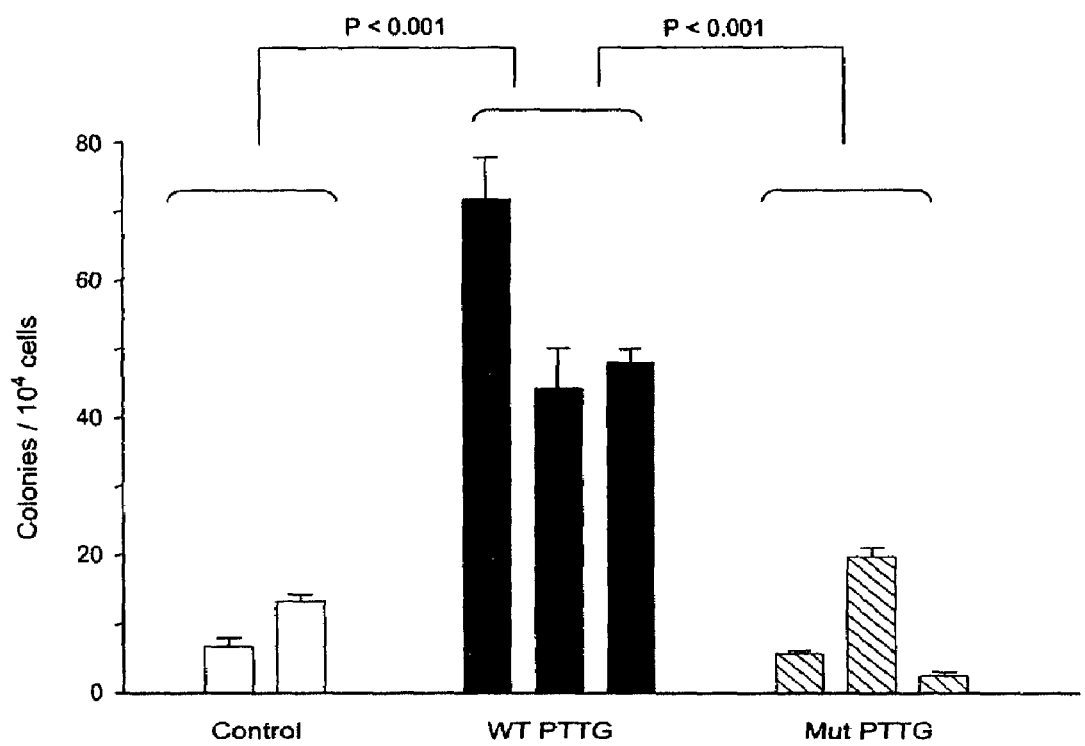
FIGS. 2D and 2E illustrate colony formation of PTTG-expressing FRTL5 cells in soft agar. Each transfectant cell line was seeded in three different plates, and colonies were counted on the 14th day. Only colonies consisting of 40 or more cells were counted. FRTL5 cells were transfected with vector only (control), or vector comprising either Wt-PTTG or mutant PTTG (i.e., PXXP motif mutated: P163A, P170L, P172A, and P173L).
Figure 2E:
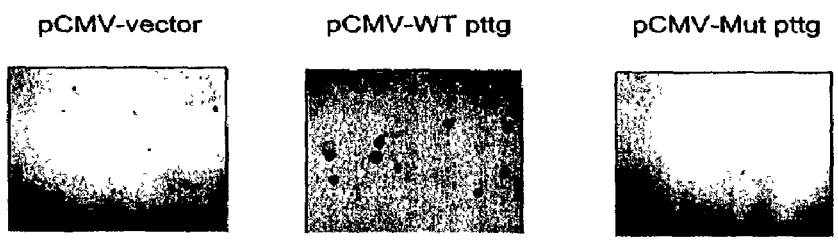

Overexpression of wild-type and mutant PTTG in transfected clones was confirmed by Northern (FIG. 2A) and Western (FIG. 2B) blot analyses. Wt-PTTG stable thyroid cell transfectants exhibited increased basic fibroblast growth factor (bFGF) expression compared with vector- or mutant-PTTG transfectants (FIG. 2C), confirming our previous observations in 3T3 fibroblasts (Zhang, X, et al., *Structure, expression and function of human pituitary transforming gene (PTTG)*, Mol. Endocrinol. 13:156–166 [1999]). The ability of these cells to undergo transformation was tested in an anchorage-independent growth assay. FRTL5 cells overexpressing wild-type PTTG formed numerous large colonies (44±6 to 72±6 colonies/plate, mean±SEM) on soft agar, compared with FRTL5 cells transfected with vector only (FIG. 2D and FIG. 2E; 7 1 to 13±1 colonies/plate; P<0.001). FRTL5 cells expressing mutant PTTG formed fewer colonies than cells overexpressing wild-type PTTG and were similar to those observed for cells transfected with vector alone (ranging from 2±0.3 to 19±1 colonies/plate; P<0.001). These results demonstrate in vitro transforming activity of human PTTG and support our previous observation that a signaling protein(s) containing an SH3 domain(s) mediates PTTG transforming action.

PTTG Over-expression is Associated with a Dedifferentiated Phenotype

Figure 3A:
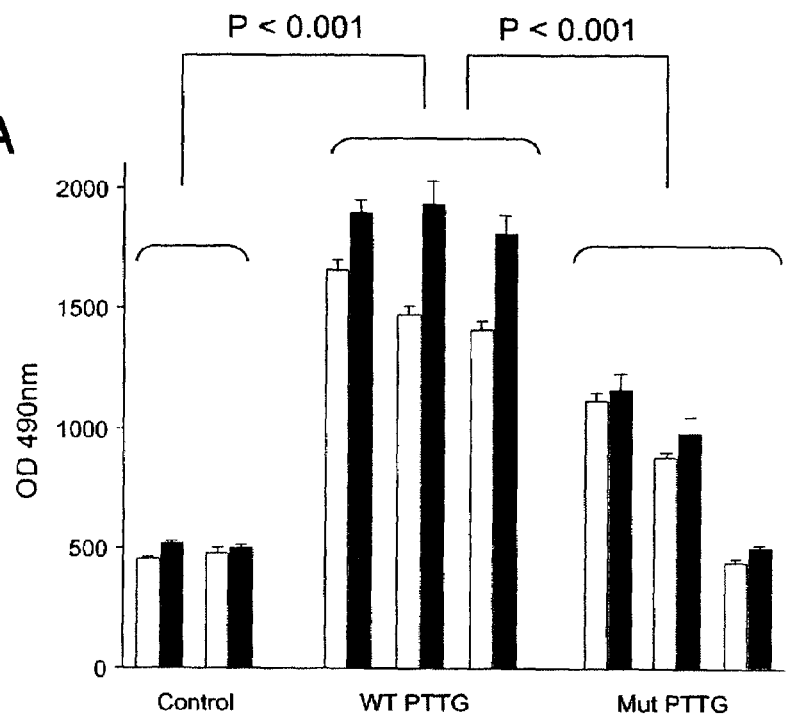
FIG. 3A shows cell growth as determined by the 3-[4,5-dimethylthiazol-2-yl]-2,5-diphenyltetrazolium bromide assay. Results at 24 hour (white bars) and 48 hour (shaded bars) are shown for individual clones (control, n=2; Wt-PTTG, n=3; mutant PTTG, n=3) in multiplicate (n=8) as the mean±SEM and compared by ANOVA. Optical density at 490 nm was measured.
Figure 3B:
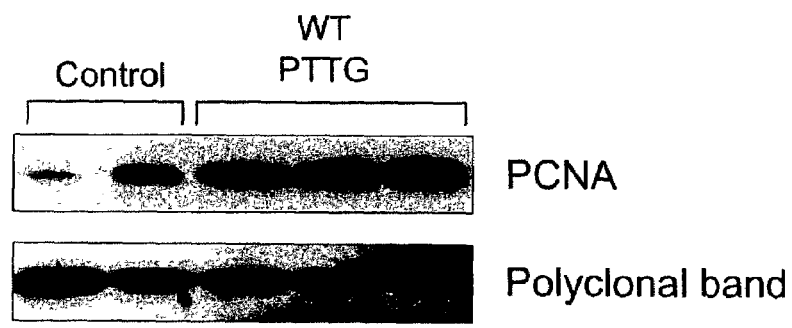
FIG. 3B, Western blot, and FIG. 3C, immunocytochemical analysis, demonstrate increased PCNA in Wt-PTTG-transfected FRTL5 cells compared with vector only- transfected controls. PCNA serves as a further indicator of cell proliferation.
Figure 3C:
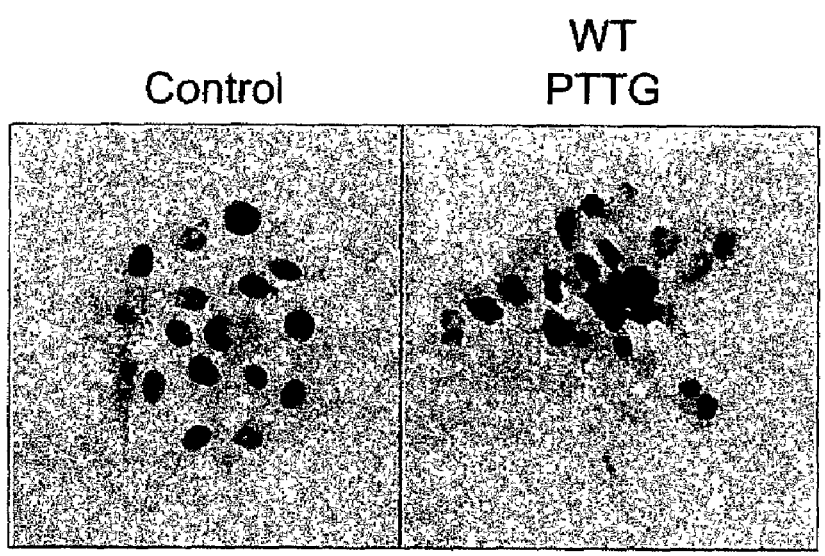
FIG. 3 illustrates that FRTL5 PTTG overexpression causes increased proliferation and is associated with a dedifferentiated phenotype. Vector control-, Wt-PTTG-, or mutant PTTG-transfected FRTL5 cells (~5000) were seeded onto 96-well plates in culture medium (see Examples).
FIG. 3D demonstrates decreased Tg expression in Wt-PTTG-transfected FRTL5 cells compared with vector- and mutant-PTTG-transfected controls.
Figure 3D:
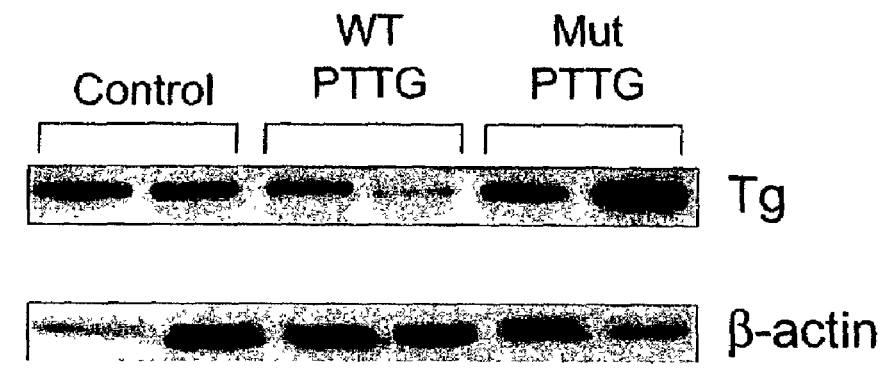

FRTL5 cells transfected with wild-type PTTG exhibited increased proliferation rates compared with cells transfected with vector alone (FIG. 3A and FIG. 3B; P<0.001). Cells transfected with PTTG constructs harboring mutations in the proline-rich region exhibited an intermediate proliferation rate, which was higher than vector-only-transfected controls (FIG. 3A; P<0.001). In keeping with the enhanced proliferation of these cells, Western blot demonstrated increased PCNA expression in wild-type PTTG transfectants (FIG. 3B), and immunohistochemistry confirmed that some cells exhibited intense PCNA immunostaining (FIG. 3C). PCNA serves as a further indicator of the occurrence of cell proliferation, thereby further evidenceing the increased proliferation rate of cells transfected with wild-type PTTG as compared to cells transfected with vector alone. We examined Thyroglobulin (Tg) levels in the PTTG-transfected cells as a marker of a differentiated thyrocyte. (Malthiery, Y., et al., *Primary structure of human thyroglobulin deduced from the sequence of its 8448-base complementary DNA*, Eur. J. Bio-Chem. 165:491–498 [1987]). Rat thyrocytes overexpressing wild-type PTTG-expressed lower Tg levels than thyrocytes transfected with mutant-PTTG or vector alone (FIG. 3D).

Thyroidal PTTG Over-expression Causes Reduced Iodide Uptake

Figure 4A:
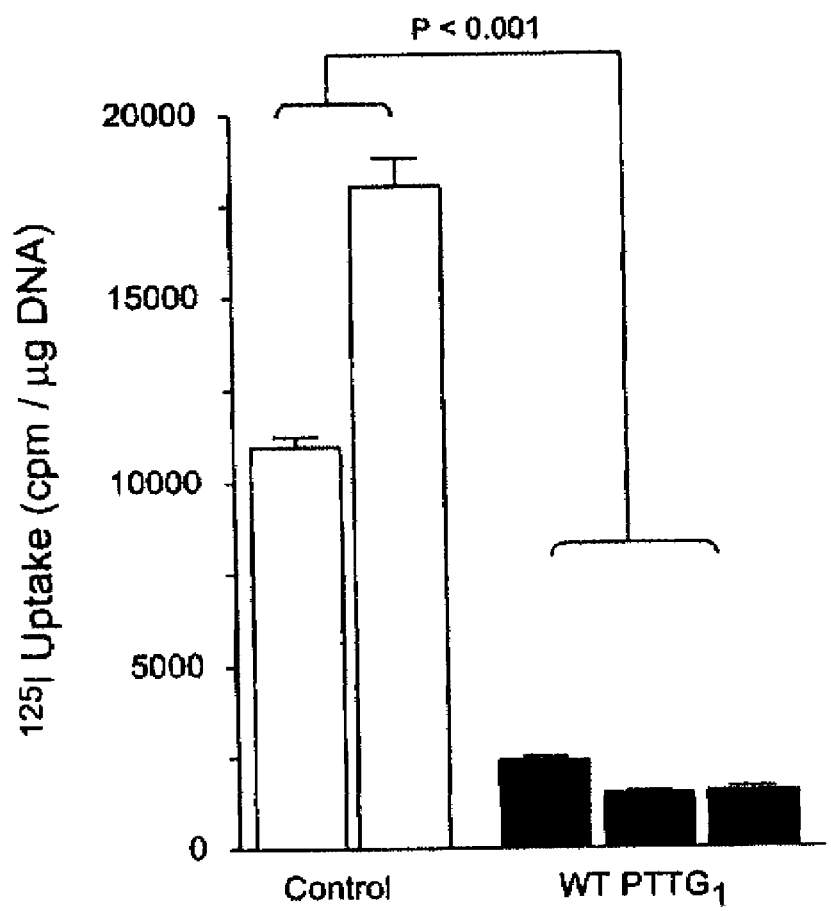
FIG. 4A depicts the results of the measurement of total DNA content in each well; these results are expressed as the mean±SEM counts per min/μg DNA. All experiments were performed multiple times (eight wells for each clone) on two separate occasions, and results were compared by ANOVA. Figure B depicts the Northern blot analysis, which illustrates NIS and β-actin mRNA expression in vector- and Wt-PTTG-transfected FRTL5 cells.
Figure 4B:
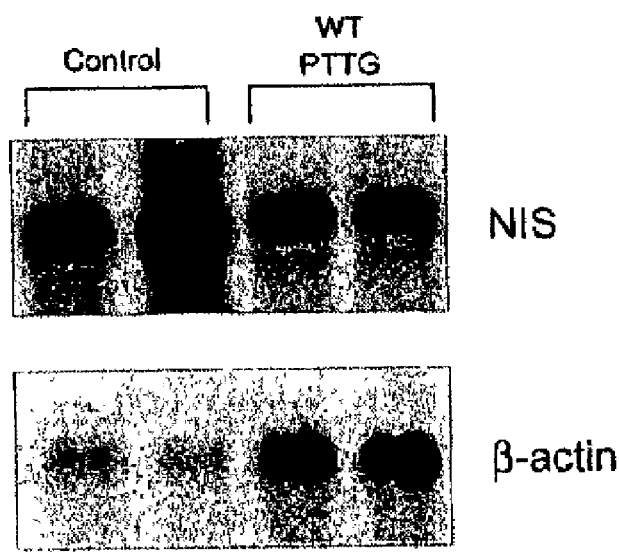
FIG. 4 illustrates how thyroidal PTTG overexpression causes reduced iodide uptake and reduced NIS mRNA expression. Vector- and Wt-PTTG-transfected FRTL5 cells ($2 \times 10^5$) were seeded onto 24-well plates, and iodide uptake was assayed after the addition of 0.1 μCi carrier-free [$^{125}$I]-NaI for 60 min at 37° C.
FIG. 4C depicts the Iodide uptake determined after bFGF (5–10 ng/mL) treatment of FRTL5 cells as compared against vector-only trasfectants.
FIG. 4D compares Iodide uptake in vector only- and Wt-PTTG-transfected human thyroid cells. *, P<0.05; **, P<0.001.
Figure 4C:
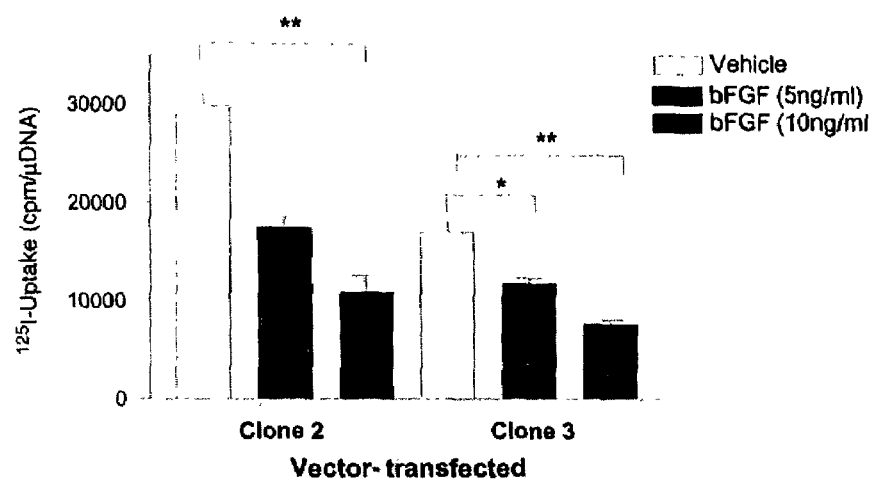
Figure 4D:
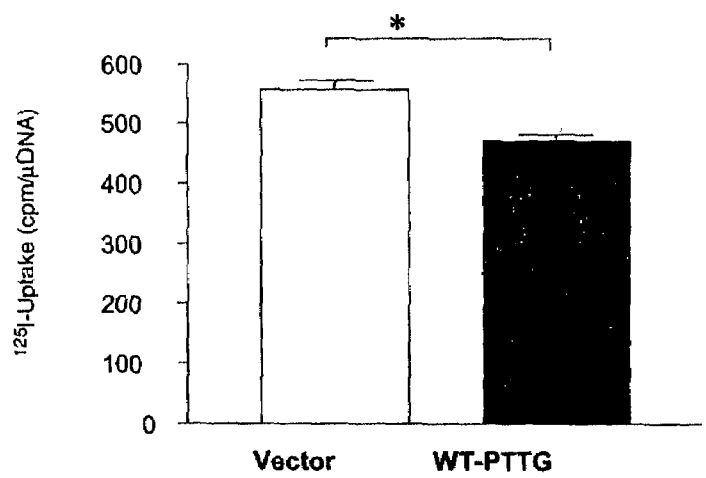

Rat FRTL5 cells overexpressing wild-type $PTTG_1$ exhibited decreased $^{125}I$ uptake compared with vector-transfected controls (FIG. 4A; P<0.001). Sodium/iodide symporter (NIS) expression in these cells was examined via Northern blot analysis and it was found that thyrocytes overexpressing wild-type $PTTG_1$ have reduced NIS expression compared with vector-transfected controls (FIG. 4B), providing a mechanism for the reduced $^{125}I$ uptake. Treatment of parental Jul. 1, 2002 10:07 AMor vector-transfected FRTL5 cells with bFGF (5–10 ng/ml) for 48 hours led to a 50% decrease in $^{125}I$ uptake (FIG. 4C; P<0.001) similar to PTTG-transfected cells, suggesting that the observed PTTG-mediated phenotypic alterations are due to secreted bFGF acting in a paracrine/autocrine manner. Transient overexpression of Wt-PTTG in normal human thyroid cells in vitro led to a 10% decrease in $^{125}I$ uptake (FIG. 4D; P=0.02), extending and confirming our observations in the stably transfected FRTL5 cells.

PTTG is Induced by Thyroid Growth Factors

TSH treatment (5–25 μ/mL) of cultured rat FRTL5 cells or primary human thyroid cells induced pttg expression in vitro (pttg increase, 5.9- and 2.4-fold, respectively; P=0.01; FIG. 5A and FIG. 5B).

Administration of estrogen (1000 ng/48 h) by mini-osmotic pump infusion to Fischer 344 rats (n=3 for each group) induced rat thyroidal pttg (FIG. 5C; pttg increase, 5.3-fold). Estradiol-mediated thyroidal pttg induction was abrogated by coadministration of the anti-Estradiol 4-hydroxytamoxifen (860 μg/48 h; pttg increase, 2.4-fold).

While the invention has been described in detail with reference to certain preferred embodiments thereof, it should be understood by those of skill in the art that modifications and variations to the embodiments and exemplary disclosure provided, are within the spirit and scope of the invention as described and claimed in this patent.

What is claimed:

1. An isolated thyroid stimulating hormone (TSH)-sensitive cell transfected with an expression vector comprising:
   a DNA segment having a polynucleotide sequence encoding a functional pituitary tumor transforming gene (PTTG) peptide that has the amino acid sequence SEQ ID NO:4,
   wherein the cell overexpresses a functional PUG peptide in response to TSH.

2. The thyroid stimulating hormone (TSH)-sensitive cell of claim 1, wherein said cell is an FRTL5 cell.

3. The thyroid stimulating hormone (TSH)-sensitive cell of claim 1, wherein said expression vector is a pCiNeo expression vector comprising said DNA segment.

4. The thyroid stimulating hormone (TSH)-sensitive cell of claim 1, wherein the cell overexpresses a functional PUG peptide in response to estrogen.

5. An in vitro cell model for the study of the effects of PTTG over-expression in a mammalian cell, comprising the isolated thyroid stimulating hormone (TSH)-sensitive cell of claim 1.

6. The in vitro cell model of claim 5, wherein exposing the cell to estrogen induces expression of a functional PTTG peptide from said expression vector.

7. An isolated thyroid stimulating hormone (TSH)-sensitive cell transfected with an expression vector wherein the vector is transfected with a DNA segment having a polynucleotide sequence encoding a functional pituitary tumor transforming gene (PTTG) peptide, having an amino acid sequence selected from the group consisting of:
   (a) SEQ ID NO:4; and
   (b) SEQ ID NO:4 comprising mutations P163A, P170L, P172A, and P173L,
   wherein the cell overexpresses a functional PTTG peptide in response to TSH.

8. The thyroid stimulating hormone (TSH)-sensitive cell of claim 7, wherein said cell is an FRTL5 cell.

9. The thyroid stimulating hormone (TSH)-sensitive cell of claim 7, wherein said expression vector is a pCiNeo expression vector comprising said DNA segment.

10. The thyroid stimulating hormone (TSH)-sensitive cell of claim 7, wherein the cell overexpresses PTTG in response to estrogen.

11. An in vitro cell model for the study of the effects of PTTG over-expression in a mammalian cell, comprising the isolated thyroid stimulating hormone (TSH)-sensitive cell of claim 7.

12. The in vitro cell model of claim 11, wherein exposing the cell to estrogen induces expression of a functional pituitary tumor transforming gene (PTTG) peptide from the expression vector.

* * * * *